US010533932B2

(12) United States Patent
Guldberg et al.

(10) Patent No.: US 10,533,932 B2
(45) Date of Patent: Jan. 14, 2020

(54) APPARATUS AND METHODS FOR LIQUID SEPARATION AND CAPTURE OF BIOLOGICS

(71) Applicant: Cancer Research Technology Limited, London (GB)

(72) Inventors: Per Guldberg, Copenhagen (DK); Kenneth Eric Steven, London (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 0 days.

(21) Appl. No.: 15/927,015

(22) Filed: Mar. 20, 2018

(65) Prior Publication Data

US 2018/0224362 A1 Aug. 9, 2018

Related U.S. Application Data

(63) Continuation-in-part of application No. 15/021,470, filed as application No. PCT/GB2014/052776 on Sep. 12, 2014, now abandoned.

(30) Foreign Application Priority Data

Sep. 13, 2013 (GB) .................................. 1316347.2

(51) Int. Cl.
*G01N 1/40* (2006.01)
*C12Q 1/6806* (2018.01)
(Continued)

(52) U.S. Cl.
CPC ........... *G01N 1/4077* (2013.01); *B01D 71/48* (2013.01); *B01L 3/502* (2013.01); *C12Q 1/6806* (2013.01);
(Continued)

(58) Field of Classification Search
None
See application file for complete search history.

(56) References Cited

U.S. PATENT DOCUMENTS 4,376,053 A 3/1983 Bullock et al.
4,829,005 A 5/1989 Friedman et al.
(Continued)

FOREIGN PATENT DOCUMENTS

GB 1311457 A 3/1973
JP S55-041896 A 3/1980
(Continued)

OTHER PUBLICATIONS

Birkhahn, M. et al., A novel precision-engineered microfiltration device for capture and characterization of bladder cancer cells in urine, European Journal of Cancer (2013).
(Continued)

*Primary Examiner* — Xiaoyun R Xu
(74) *Attorney, Agent, or Firm* — Choate, Hall & Stewart LLP

(57) ABSTRACT

The present disclosure provides apparatus and methods for processing liquids or fluids. Such apparatus and methods are convenient and efficient for low-cost separation, filtration, capture, collection, and/or storage of biologics and related materials. Provided apparatus and methods are designed for point-of-care use and offer advantages for patients and medical practitioners, including advantages in diagnosis and long-term monitoring of conditions.

20 Claims, 10 Drawing Sheets

(51) Int. Cl.
  *B01L 3/00* (2006.01)
  *B01D 71/48* (2006.01)
  *C12Q 1/6886* (2018.01)
  *B01D 61/14* (2006.01)
  *B01D 63/08* (2006.01)
  *B01D 71/50* (2006.01)

(52) U.S. Cl.
  CPC .......... *C12Q 1/6886* (2013.01); *B01D 61/147* (2013.01); *B01D 63/087* (2013.01); *B01D 71/50* (2013.01); *B01D 2313/025* (2013.01); *B01L 2200/0631* (2013.01); *B01L 2200/16* (2013.01); *B01L 2300/041* (2013.01); *B01L 2300/045* (2013.01); *B01L 2300/047* (2013.01); *B01L 2300/049* (2013.01); *B01L 2300/0681* (2013.01); *B01L 2300/087* (2013.01); *B01L 2300/0816* (2013.01); *B01L 2300/0832* (2013.01); *B01L 2300/12* (2013.01); *B01L 2400/0478* (2013.01); *C12Q 2600/154* (2013.01); *C12Q 2600/156* (2013.01); *C12Q 2600/158* (2013.01); *G01N 2001/4088* (2013.01)

(56) References Cited

U.S. PATENT DOCUMENTS

| | | | |
|---|---|---|---|
| 5,077,012 A * | 12/1991 | Guirguis | A61B 10/0045 422/401 |
| 5,139,031 A | 8/1992 | Guirguis | |
| 5,224,489 A | 7/1993 | Guirguis | |
| 5,471,994 A | 12/1995 | Guirguis | |
| 5,484,572 A | 1/1996 | Katakura et al. | |
| 5,846,487 A | 12/1998 | Bennett, II | |
| 5,849,505 A | 12/1998 | Guirguis | |
| 6,176,836 B1 | 1/2001 | Trudil et al. | |
| 6,733,250 B2 | 5/2004 | Yajima | |
| 7,846,393 B2 | 12/2010 | Tai et al. | |
| 7,846,743 B2 | 12/2010 | Tai et al. | |
| 8,288,170 B2 | 10/2012 | Tai et al. | |
| 2009/0306610 A1 | 12/2009 | Van Den Heuvel et al. | |
| 2016/0223442 A1 | 8/2016 | Guldberg et al. | |

FOREIGN PATENT DOCUMENTS

| WO | WO-2006/116327 A1 | 11/2006 |
| WO | WO-2010/131140 A1 | 11/2010 |
| WO | WO-2011/111386 A1 | 9/2011 |
| WO | WO-2013/022974 A1 | 2/2013 |
| WO | WO-2014/081877 A1 | 5/2014 |

OTHER PUBLICATIONS

Bostwick, I. et al., Improved Filter Method for Urine Sediment Detection of Urothelial Carcinoma by Fluorescence In Situ Hybridization, Arch. Pathol. Lab. Med., 131: 1574-1577 (2007).

GB Search Report under Section 17 for GB1316347.2, 2 pages (dated Mar. 13, 2014).

International Search Report of PCT/GB14/52776, 4 pages (dated Dec. 16, 2014).

Lin, H.K. et al., Portable Filter-Based Microdevice for Detection and Characterization of Circulating Tumor Cells, Clin. Cancer Res., 16(2): 5011-5018 (2010).

Villicana, P. et al., Urine-based assays for the detection of bladder cancer, Biomark Med., 3(3): 265 (2009).

Written Opinion of PCT/GB14/52776, 6 pages (dated Dec. 16, 2014).

Zheng, S. et al., Membrane microfilter device for selective capture, electrolysis and genomic analysis of human circulating tumor cells, Journal of Chromatography A, 1162: 154-161 (2007).

* cited by examiner

APPARATUS AND METHODS FOR LIQUID SEPARATION AND CAPTURE OF BIOLOGICS

CROSS-REFERENCE TO RELATED APPLICATIONS

This patent application is a Continuation-In-Part of U.S. patent application Ser. No. 15/021,470, filed on Mar. 11, 2016, which is a national stage entry of international patent application no. PCT/GB2014/052776, filed on Sep. 12, 2014, which application claims priority benefit of, GB 1316347.2 which was filed on Sep. 13, 2013, the entire contents of each of which are hereby incorporated by reference herein.

FIELD OF THE INVENTION

The present invention relates to biological fluid filtration assemblies and to methods of using such assemblies.

BACKGROUND OF THE INVENTION

Bladder cancer is the sixth most common cancer in the world. The symptoms include microscopic or macroscopic hematuria, painful urination and polyuria; however, none of these symptoms is specific for the disease. The gold standard for diagnosing bladder cancer is cystoscopy and subsequent transurethral resection of the bladder tumour (TURBT). The sensitivity of cystoscopy for non-muscle invasive bladder cancer (NMIBC; stage Ta, T1 and Tis) is around 80% with white-light cystoscopy and >95% with fluorescence (hex-aminolevulinate)-guided cystoscopy.

The majority of bladder tumour patients (70-80%) are diagnosed with NMIBC, which has a relatively good prognosis. However, the recurrence rate for these tumours is very high, with around 70 of the patients experiencing relapses, and up to 25% of these recurrences will progress to muscle invasive cancers (MIBC; stage T2-4) with a poor prognosis. The high recurrence rate and the risk of progression require life-long surveillance with periodic cystoscopy, making bladder cancer the most expensive cancer to treat (Avritscher et al., 2006). As less than 10% of all patients presenting with microscopic or visible hematuria will be diagnosed with bladder cancer, the number of cystoscopies performed to rule out bladder cancer is high and places a considerable burden on the healthcare system. Moreover, as cystoscopy is an invasive method that causes considerable discomfort to the patients, there is an unmet need for noninvasive techniques for reliable and cost-effective diagnosis and surveillance of bladder cancer.

Voided urine from bladder tumour patients may contain exfoliated tumour cells that can be identified by cytology. Urine cytology has been used for decades and is still the most common noninvasive technique for detection of bladder tumours. However, it has a low sensitivity for detection of NMIBC (10-20%) Several alternative non-invasive tests have been developed, including some that have been approved by the U.S. Food and Drug Administration (FDA): Bladder tumour antigen assay, NMP22, ImmunoCyt and Urovysion. To date, none of these tests has achieved widespread use in clinical practice due to low specificity (Liou, L. S. (2006). Urothelial cancer biomarkers for detection and surveillance. Urology 67, 25-33; Tetu, B. (2009). Diagnosis of urothelial carcinoma from urine. Mod. Pathol. 22 Suppl 2, S53-S59; Wadhwa, N., Jatawa, S. K., and Tiwari, A. (7017) Non-invasive urine based tests for the detection of bladder cancer. J. Clin. Pathol. 65. 970-975.).

Bladder tumour cells contain a large number of genome alterations, including gross chromosomal aberrations, amplifications, deletions, single nucleotide substitutions and aberrant DNA methylation. Only a minority of the changes found in individual tumours may be required for initiating and maintaining neoplastic growth ("drivers"), with the remainder being "passenger" events that have no or little effect on the malignant phenotype. Both driver and passenger events may have a potential as biomarkers for bladder cancer, provided that they are cancer specific (i.e., not found in normal tissues or present at a different level of expression) and recurrent (i.e., occur in independently arising tumours at appreciable frequencies).

The most frequently mutated genes in bladder cancer include the proto-oncogenes FGFR3, RAS, and PIK3CA, and the tumour suppressor gene TP53. Mutations in FGFR3 are common in NMIBC, with reported frequencies of >60%, whereas TP53 mutations are predominantly found in MIBC. In addition, hundreds of genes have been shown to be differentially methylated between bladder tumours and normal bladder epithelium.

Studies over the last decade have shown that it is possible to detect bladder tumour-specific genome alterations in DNA isolated from urine sediments. The sensitivity and specificity of DNA-based bladder tumour detection vary considerably among studies, depending on the patient population, the choice of DNA biomarkers and the methods employed for detecting these biomarkers. Some studies have reported diagnostic sensitivities close to or above 90% and specificities close to 100% (Dulaimi et al (2004). Detection of bladder cancer in urine by a tumor suppressor gene hypermethylation panel. Clin. Cancer Res. 10, 1887-1893; Costa er al (2010). Three epigenetic biomarkers, GDF15, TMEFF2, and VIM, accurately predict bladder cancer from DNA-based analyses of urine samples. Clin. Cancer Res. 16, 5842-5851; Hoque et al (2006). Quantitation of promoter methylation of multiple genes in urine DNA and bladder cancer detection. J. Natl. Cancer Inst. 98, 996-1004; Reinert et al (2011). Comprehensive genome methylation analysis in bladder cancer: identification and validation of novel methylated genes and application of these as urinary tumor markers. Clin. Cancer Res. 17, 5582-5592). A recent study has suggested that analysis of DNA biomarkers in urine can also be used to monitor recurrence and reduce the number of cystoscopies in low-risk patients with no concomitant tumour (Reinert et al (2012). Diagnosis of bladder cancer recurrence based on urinary levels of EOMES, HOXA9, POU4F2, TWIST1, VIM, and ZNF154 hypermethylation. PLoS. One. 7, e46297). With the advent of improved methods for detection of low-abundant, tumour-specific DNA, including third-generation PCR (digital PCR) and next-generation sequencing, the potential of urine-based detection of bladder tumours has increased dramatically.

One of the main challenges when using urinary DNA markers for diagnosis and surveillance of bladder cancer is to obtain a sufficient number of cells for downstream analysis. In some studies, up to 35% of the samples have been excluded from analysis due to insufficient amounts of DNA (Reinert et al., 2012). The number of tumour cells exfoliated into the urine shows a high inter- and intra-individual variability. In general, the number of cells released correlates with tumour size and stage, such that small early-stage tumours will release fewer cells than MIBC. This limits the usefulness of urinary DNA markers in the non-invasive detection and monitoring of disease and disease progression.

SUMMARY OF THE INVENTION

The present invention is based on the inventors' insight that a convenient and efficient assembly for capturing and storing biological material obtained from biological fluids may offer significant advantages for patients and medical practitioners in the diagnosis and long-term monitoring of conditions and disorders.

Broadly, the present invention relates to filtration assemblies for easy and low-cost collection of biological material from biological fluids and to methods using these filtration assemblies. The present invention further relates to assemblies for the storage of biological material collected from such fluids, and methods of using the same.

The provision of assemblies for easy and low-cost collection of biological material from biological fluids which may, for example, be provided to a patient for use at home, offers significant advantages to patients. The captured material may be immediately stored, either for later provision to an analyst or medical practitioner at an appointment, or mailed to an appropriate medical centre or testing facility for analysis through a mail carrier.

Assemblies of the present invention also offer advantages in the provision of medical care in a patient's home by visiting medical practitioners and carers. Captured material may be stored immediately, either for mailing to an appropriate medical centre or testing facility or transport there by the medical practitioner or carer. Assemblies of the present invention also offer advantages in the provision of medical care during clinic or hospital visits and/or stays.

For example, assemblies and methods described herein may be of relevance to the collection and filtering of urine for the capture and detection of cells associated with genitourinary disorders. These disorders may include genitourinary cancers such as for example, and not by way of limitation, bladder, prostate and renal cancer. These disorders may also include gynecological cancers such as endometrial cancer or cancers that have metastasized to the genitourinary site from other sites.

Uses of the assemblies described herein directed to urine filtration were prompted by the inventors' insights into the limitations of current procedures for bladder tumour diagnosis and the disadvantages of cystoscopy, which is commonly used for the diagnosis and long-term monitoring of patients, both in terms of discomfort to the patient and the burdens placed by this approach on health care systems.

However, cells and other biological material, associated with urological disorders other than cancer may also be captured and stored using assemblies of the present invention.

It will be appreciated that assemblies of the invention may also be used for the collection of cells (such as for example, and not by way of limitation, normal epithelial, cancer, bacterial or yeast cells) and other biological material (such as for example, and not by way of limitation, proteins or nucleic acids) from other biological samples, such as for example, and not by way of limitation, saliva, sera, blood, and washes, for example, bladder washes.

The assembly may comprise a filtration device and a storage unit. The method may comprise an initial step of capturing biological material by forcing fluid through a filter that is housed in a support, for example, a removable filter cartridge. After filtration, the support with filter content can be removed from the filtration device and placed into the storage unit, which may contain an appropriate solution for facilitating storage and/or analysis of the captured biological material.

Accordingly, in a first aspect the present invention may provide a biological fluid filtration assembly comprising a filtration device for filtering a biological fluid sample, and a storage unit, the filtration device having a collection chamber, a waste reservoir, and a filter support platform, the filter support platform housing a removable filter cartridge having a filter suitable for capturing biological material present in the biological fluid sample; wherein the collection chamber, waste reservoir and filter support platform are connectable to permit passage of a biological fluid from the collection chamber into the waste reservoir through the filter of the filter cartridge; and the storage unit having a body configured to engage with the removable filter cartridge such that, when engaged, the filter of the filter cartridge is sealed within the body of the storage unit.

The filter cartridge may be slidably retained in the filter support platform. That is, the filter support platform may have a recess of a size and shape suitable for receiving the filter cartridge such that, when the filter cartridge is inserted, the filter is positioned as described so that, in use, fluid passes from the collection chamber into the waste reservoir through the filter. This slidable engagement may be provided with complementary protrusions and recesses on the filter cartridge and in the recess to improve the fit and hold and/or to provide a snap fit-type interaction to prevent accidental removal of the filter cartridge in use.

The storage unit body may comprise a recess for slidably receiving the filter cartridge. Preferably, the recess of the storage unit body is configured to engage with the filter cartridge such that the filter cartridge may not be removed accidentally. This may be through use of a sufficiently close fit, or by the provision of complementary protrusions and recesses on the filter cartridge and in the recess to improve the fit and hold and/or to provide a snap fit-type interaction to retain the filter cartridge in place.

The storage unit body may have an opening to permit access to the filter and/or filter content of the filter and/or a liquid surrounding the filter when the filter cartridge is in place. Thus, the storage unit may further comprise a removable lid covering the opening. It will be appreciated that depending on the intended use and on the nature of the lid, in some embodiments the lid may be arranged to provide access only to the filter content, that is, the biological material trapped on the filter following use, or to the filter content and/or any surrounding liquid following use.

For some applications, it may be preferable for the captured biological material to be exposed to a solution prior to analysis. This may facilitate analysis and/or improve storage. A suitable solution may, for example, be a buffer suitable for inducing cell lysis, a fixative/preservative, a culture medium, an isotonic buffer, or an appropriate buffer for elution, each as described herein. It will be appreciated that the provision of a solution chamber, and the inclusion of a solution, is an optional feature.

Accordingly, in some embodiments, the storage unit is arranged such that the lid has a solution chamber containing a solution selected to facilitate storage and/or analysis of the biological material, wherein engagement of the lid with the storage unit body causes the solution to be released such that it contacts the filter. It will be appreciated that for assemblies having such an arrangement, after filtration and capture of biological material on the filter, the filter cartridge may be inserted into the storage unit without the lid in place. The lid may then be fitted, thereby releasing the solution.

The storage unit may alternatively be configured to have a solution chamber arranged such that engagement of the filter cartridge with the storage unit causes the release of the solution into contact with the filter. In some preferred embodiments, the storage unit has a piston retained within the recess, the piston and recess defining a solution chamber distal from the recess opening, the solution chamber containing a solution selected to facilitate storage, processing and/or analysis of the biological material, the piston being configured such that insertion of the filter cartridge into the recess causes the piston to move further in to the recess, such that the solution contained within the chamber is forced around the piston into contact with the filter, are therefore with any filter content present. The storage unit may be provided with a solution in place in the chamber, or may be provided separately for inclusion in the storage unit by a user. Accordingly, access to the solution chamber may be permitted by removal of a lid.

While it will be appreciated that assemblies described herein may be used to filter biological fluids using only gravity, that is, through gravitational percolation, it is preferable to provide a means of, or for, facilitating passage of the biological liquid through the filter. This may be achieved by creating a pressure differential, for example, by providing means for applying pressure to the liquid in the collection chamber to push the biological fluid through the filter, or by providing means for creating a vacuum in the waste reservoir to pull the biological fluid through the filter.

Preferably, the filtration device has means to enable application of pressure to a fluid contained within the collection chamber when the device is assembled to force the fluid through the filter into the waste reservoir. The collection chamber may itself be compressible such that when the filtration device is assembled and the collection chamber contains a fluid sample, compression of the collection chamber applies pressure to the fluid, thereby forcing the fluid through the filter into the waste reservoir. For example, the collection chamber may be a cylindrical bag with a spring surrounding the cylindrical bag along its cylindrical axis, thereby permitting compression of the cylindrical bag in the direction of its cylindrical axis.

However, alternative arrangements may be used. For example, the collection chamber may be provided with a piston configured to force biological fluid through the filter from the collection chamber to the waste reservoir when the filtration device is assembled following sample provision. A pump system may also be used to apply pressure.

In an alternative arrangement, means may be provided for generating a vacuum to pull/suck the fluid through the filter. This may be through use of a pump arranged to draw air out of the waste reservoir, thereby creating a vacuum, or the waste reservoir may itself be provided with chamber under vacuum. This chamber may then be opened to the remainder of the waste reservoir, for example by releasing a valve, to draw the fluid through the filter during filtration.

If a pressure differential is to be used to force/draw the biological fluid through the filter, it may be desirable to include one or valves configured to allow pressure within the device to equilibrate during and after application of pressure/vacuum.

While it will be appreciated that assemblies of the present invention are applicable to the filtration of many biological fluid samples as described herein, in some preferred embodiments the biological fluid is urine or a bladder wash, most preferably urine. In some other embodiments, the fluid may be blood or serum. The waste reservoir may contain an absorbent and/or deodorising material, which may be especially advantageous for the filtration of urine samples.

The filter may be selected to capture biological material as desired and as described herein. Preferably, the filter is selected to capture biological material associated with the diagnosis and/or prognosis of a disease, condition or disorder, for example, with cancer. In some preferred embodiments the biological material is cells suspended in the biological fluid, more preferably, cells suspended in urine.

The biological material may be tested for the presence of, for example, markers associated with the diagnosis and/or prognosis of a disease, condition or disorder. The biological material may be cells suitable for testing for the presence of a marker that is indicative of a particular disease, condition or disorder, for example, markers associated with the diagnosis and/or prognosis of urological cancers.

In a further aspect, the present invention may provide method of capturing biological material from a biological sample using an assembly as described herein, the method comprising:
 (i) providing a biological fluid sample into the collection chamber;
 (ii) connecting the collection chamber to the filter support platform and waste reservoir;
 (iii) causing the biological fluid sample to flow from the collection chamber into the waste reservoir through the filter to capture biological material present in the fluid; and
 (iv) removing the filter cartridge from the filter support platform and inserting the filter cartridge into the storage unit.

The method may further comprise the step of applying pressure to the biological fluid sample in the collection chamber to force flow of the biological fluid sample from the collection chamber into the waste reservoir through the filter, for example, by compressing the collection chamber, if the assembly is suitably arranged. Alternatively, the method may further comprise the step of generating a vacuum within the waste reservoir to suck the biological fluid sample through the filter.

The filter cartridge and storage unit combination may provide a convenient sealed unit for storage and/or transportation of the captured biological material. For example, the filter cartridge and storage unit combination may then be stored prior to testing, given to an appropriate care giver, for example, a medical practitioner, or transported using, for example, a national mail carrier or internal mail system, in each case conveniently and hygienically.

Once received by an analyst, the captured biological material may be retrieved from the filter and/or any surrounding liquid and tested as described herein. This testing may assist in the diagnosis and/or prognosis of conditions as described herein.

Accordingly, in a further aspect the present invention provides a method wherein, having filtered a biological fluid sample using an assembly and/or method as described herein, a method comprising the steps of
 (i) isolating nucleic acids, proteins or cells from the biological material captured on the filter and/or in the solution if present; and
 (ii) testing the isolated material for markers known to be associated with a particular disease, condition or disorder.

It will be appreciated that assemblies as described herein will typically be provided to a user, who may be the patient themselves or an appropriate care giver such as a medical practitioner, in a kit form. Accordingly, in a further aspect the present invention provides a kit comprising a collection chamber, a filter support platform, a waste reservoir, and a storage unit, as any one embodiment described herein, and, optionally, instructions for a method as described herein.

It will be appreciated that in some circumstances, the individual elements of the assembly may be provided separately, and that the invention also provides a filter cartridge as described herein and a storage unit as described herein which may be supplied separately to the remainder of the assembly.

The present invention includes any combination of the aspects and preferred features described herein except where such a combination is clearly impermissible or expressly avoided.

BRIEF DESCRIPTION OF THE FIGURES

Embodiments and methods of the present invention will now be described, by way of example, with reference to the accompanying drawings in which.

DETAILED DESCRIPTION

The following applications of the present invention are provided by way of example and not limitation.

The Assembly

Figure 1:
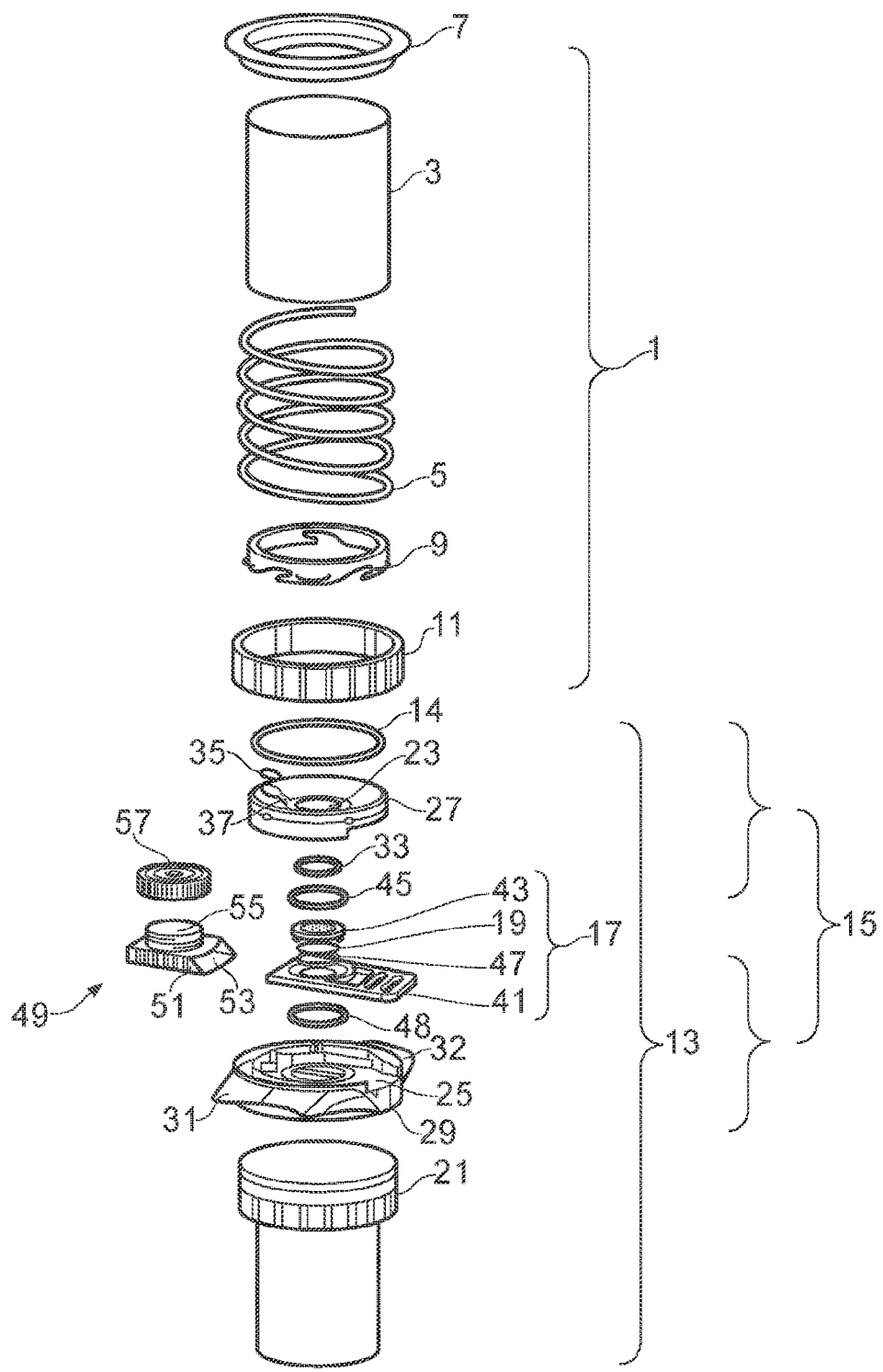
FIG. 1 shows a technical drawing showing an exploded view of a filtration assembly according to the present invention.
Figure 2:
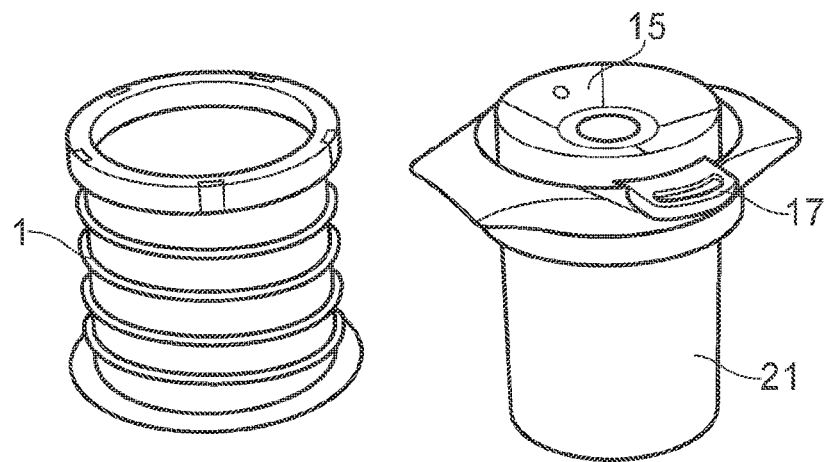
FIG. 2 shows a perspective view of a collection chamber (left) and filtration unit (right).
Figure 3:
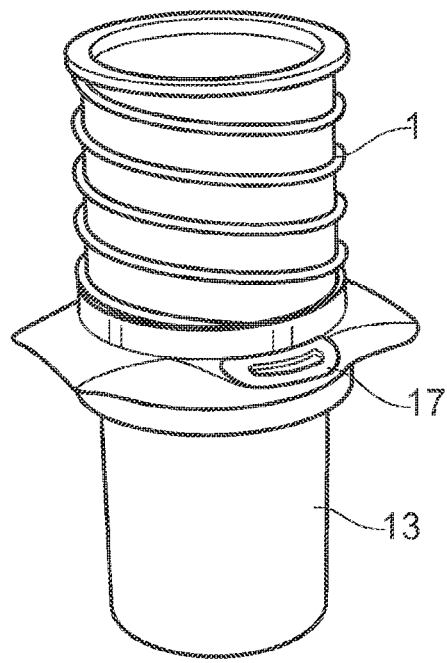
FIG. 3 shows a side view of an assembled device of the present invention.

An exploded view of an assembled biological fluid filtration assembly according to the present invention is shown in FIG. 1. The assembled device and use thereof is shown in FIG. 3, while FIG. 2 shows the collection chamber (left) and a filtration unit assembled from the filter support platform and waste reservoir (right) prior to their coupling to afford the assembled device.

The collection chamber 1 is open-topped for convenience of sample provision. The collection chamber is formed of a cylindrical bag 3 of water-impermeable material, which is approximately 100 mm in length and 95 mm in diameter and is suitable for housing a volume of approximately 500 mL for convenience of sample provision and maximal DNA when analysing urine samples. It will be appreciated that other sizes and volumes may be appropriate, both for collection of urine and other biological fluid samples. For example, for some uses sizes to accommodate volumes of 20 mL to 250 mL may be appropriate. Accordingly, in some embodiments, the collection chamber is suitable for housing up to 400 mL, 300 mL, 250 mL, 100 mL, 50 mL, or up to 20 mL. While larger volumes may be appropriate for urine collection, smaller volumes may be preferable for the filtration of, for example, saliva.

The cylindrical bag is contained within a spring 5 which imparts some rigidity to the cylindrical bag of the collection chamber. At the sealed end of the cylindrical bag is a lid 7 and at the open end of the cylindrical bag is an annular spring attachment portion 9 which encircles the open end of the cylindrical bag without substantially occluding the open portion. The spring 5 is connected to or abuts the lid 7 at one end and the annular attachment portion 9 at the other end. The lid 7 and the annular spring attachment portion 9 are rigid and made of plastics material, although other suitable rigid materials, for example, a metal such as stainless steel, may be used. The lid 7 is circular and imperforate, and of a diameter slightly larger than the diameter of the cylindrical bag. It is shaped so as to project into the volume of the cylindrical bag when assembled, although a planar lid or perforate lid may also be used. The use of a spring retained by the lid and annular spring attachment portion permits compression of the collection chamber in the direction of the cylindrical axis of the collection chamber. Other suitable means which serve the same function may also be used, for example, a series of springs surrounding the cylindrical bag or a series of telescopic rods. In these cases, bags of shapes other than cylindrical may be used. The collection chamber has a locking ring attachment 11 to which annular spring attachment portion 9 can be fixed by means of a snap fit interaction. Other fixing means may be used, including complementary screw threads and rotatably engaging lugs.

The collection chamber is connectable via the locking ring attachment 11 to the filtration unit 13 to assemble the complete filtration device. This connection is necessarily substantially watertight to permit use of the device as described herein without loss of fluid before filtration, with O-ring 14 which is retained in an annular groove around the top of the filtration unit improving the seal. The filtration unit 13 has a filter support platform 15. Small protrusions on the filter support platform 15 are located to engage with complementary indents in the annular attachment portion 9. It will be appreciated that other attachment means may alternatively be provided.

The filter support platform 15 has a removable filter cartridge 17 with a membrane filter 19, and is connectable to a waste reservoir 21. It will be appreciated that other filter materials as described herein may also be used. The waste reservoir 21 is a rigid cylindrical container made of plastics material able to accommodate a volume of at least 500 mL (that is, the entire volume of liquid contained in the collection chamber prior to filtration). Other suitable rigid materials suitable for receiving fluids may be used in place of plastics material. The waste reservoir 21 and the filter support platform 15 are connectable to form, in combination with the filter cartridge 17, the filtration unit 13. This connection is necessarily substantially watertight to permit use of the device as described herein without loss of fluid during filtration. In this embodiment, the waste reservoir 21 and the filter support platform 15 are connectable by a snap fit connection between a protrusion on the outside of waste reservoir 21 and an annular groove on the inside of the filter support platform 15. In some embodiments, the waste reservoir 21 contains a moisture absorbing material and/or a deodorant. Suitable moisture absorbing materials may include absorbent material such as paper, cotton wool or sponge, or silica gel and/or other water-absorbent polymers known in the art. The inclusion of a moisture absorbent material improves ease of disposal of the waste reservoir after use. Suitable deodorants may include carbonates such as potassium carbonate.

The exploded view shown in FIG. 1 shows the component parts of the filter support platform 15. Broadly, the filter support platform is connectable to both the connection chamber at its open end and to the waste reservoir, and when the device is fully-assembled separates the two. The filter support platform has an opening 23 to allow fluid communication between the collection chamber and the reservoir and the filter 19 of the filter support portion, in this case, filter cartridge 17, occludes this opening such that any fluid passing from the collection chamber to the waste reservoir passes through the filter. The filter support platform has a slotted recess 25 suitable for receiving a filter cartridge 17 such that the filter of the filter cartridge occludes the opening as described. The filter cartridge may be inserted and removed from the slotted recess in a sliding movement.

As shown in FIG. 1, the filter support platform is assembled from a top portion 27 and a bottom portion 29, which clip together by means of a snap-fit connection between protrusions on the top portion and complementary recesses on the bottom portion. Other connecting means may be envisaged including other snap-fit interactions and complementary screw threads. The embodiment shown in FIG. 1 has two handles, 31 and 32 to facilitate ease of use. It will be understood that handles are not necessary, and that other handle arrangements, for example, a single handle, a continuous annular handle, or one or more D-shaped handles may be used.

The top and bottom portions, 27 and 29, when fastened together, define a slot 25 suitable for receiving a filter cartridge 17 as described. O-ring 33 is provided to prevent leakage during use. The filter support platform further comprises a back flow membrane 35 and a pressure relief valve 37. The pressure relief valve is configured to activate at a certain pressure to allow liquid to pass into the waste chamber should the filter becomes saturated. The backflow membrane 35 is adapted to allow air to pass from the reservoir 21 into the collection chamber 1 during intermittence application of pressure to prevent the filter content becoming disturbed due to turbulence. There is further a small hole (not shown) in 29 that permits air to escape out of the unit entirely. In this embodiment, the relief valve is an umbrella-type valve that opens at 10-12 kg pressure, but other suitable valves may be used.

The filter cartridge 17 has a body of a width complementary to the width of the slot, and is sufficiently longer in length to cause a portion of the body to protrude from the slotted recess during use (as shown in FIG. 2) to facilitate ease of removal of the cartridge from the device. The filter cartridge housing may have one or more indentations or perforations 41 to improve grip and aid removal. The filter 19 is housed on a ledge within an opening in the filter cartridge housing and maintained in place by a perforated over support 43 which is connected to the housing by means of a snap-fit connection between protrusions on the perforated over support and complementary recesses in the housing. Other connecting means may be envisaged including other snap-fit interactions and complementary screw threads. O-rings 45, 47, and 48 improve the seal. O-ring 47 improves the seal of the assembled filter cartridge 17 around the filter 19, while O-rings 45 and 48 are present on the external surface of the filter cartridge 17 and serve both to improve the seal when the filter cartridge 17 is housed within the filter support platform for filtration of the biological fluid and to improve the seal when the filter cartridge 17 is inserted into a storage unit 49 according to the present invention.

FIG. 1 further shows such a storage unit 49 according to the present invention. The filter cartridge 17 may be inserted into the storage unit 49 after use to facilitate ease of storage and transportation and may preserve the sample during storage. The storage unit 49 further provides a means for ease of access to the filter content (and any surrounding liquid) for analysis without the need to remove the cartridge from the storage unit. Broadly, as shown in FIG. 1, the storage unit comprises a base 51 having a recess 53 suitable for receiving the filter cartridge. This base has an opening 55 located to permit access to the filter content for analysis and processing when the filter cartridge is inserted. The opening is covered by a lid 57 to preserve the sample and to permit storage and transportation. In FIG. 1 the lid connects to the base by means of complementary screw threads, although other connection means may be envisaged including a suitable snap-fit interaction or hinged lid. The lid 57 comprises a chamber containing an appropriate liquid that is released during engagement of the lid with the base 51. For example, the lid may be an OG-250 lid from Oragene®, developed by DNA Genotek® and containing a DNA lysis buffer. Base 51 has sharp protrusions which break a seal of the chamber in the lid when the lid is screwed onto the base, thereby releasing the solution. Removing the lid for analysis thereby permits access not only to the filter content but also to the contained solution in which the filter content is stored. The filter cartridge 17 and storage unit 49 form a water tight seal around the filter, the filter content, and any surrounding liquid that may be present.

Figure 4:
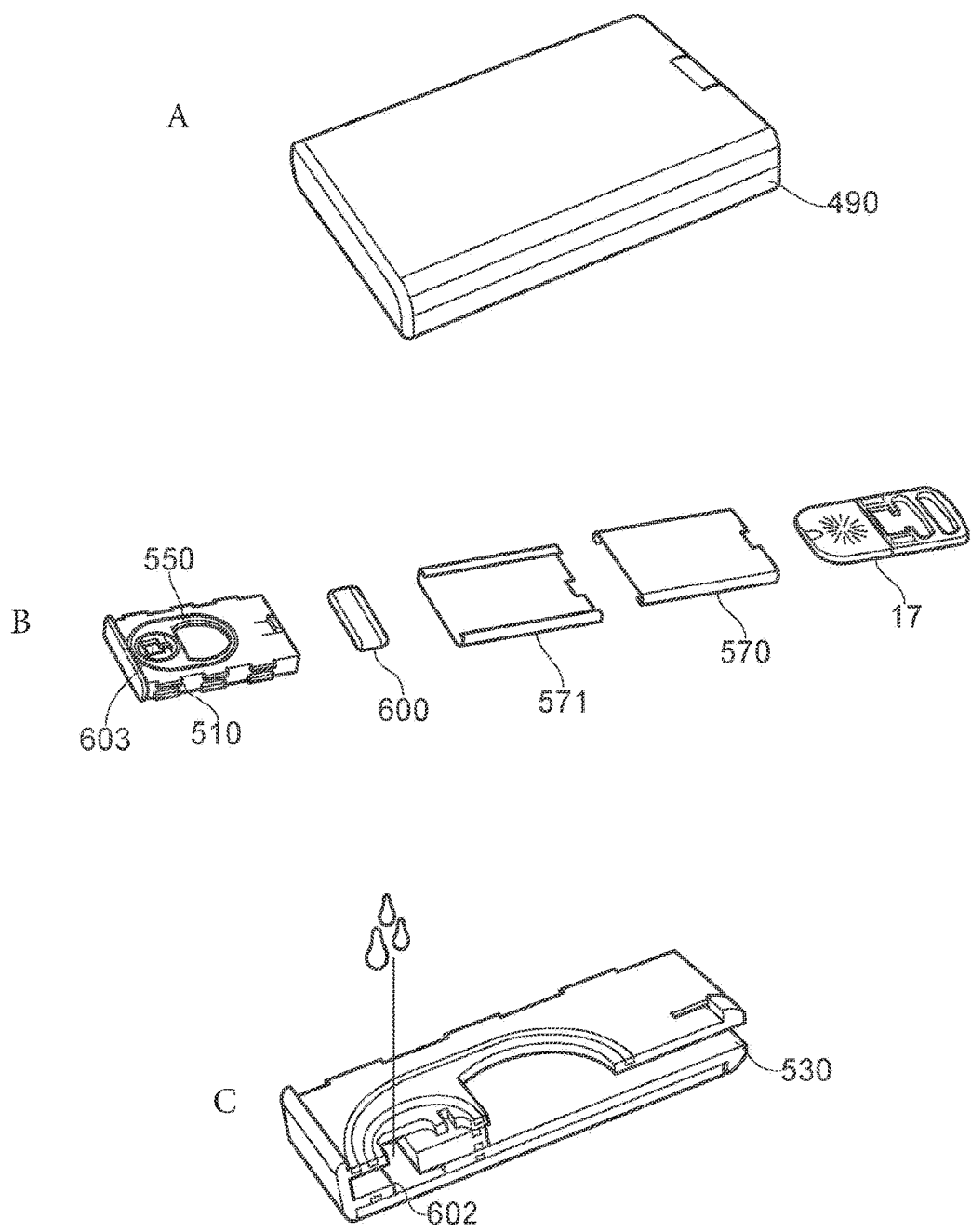
FIG. 4 shows an alternative storage unit according to the present invention, and the assembly thereof. A) shows a storage unit. B) shows an exploded view of components of a storage unit. C) shows a cross-section of a housing.

FIG. 4 shows an alternative storage unit according to the present invention, and the assembly thereof. The storage unit 490 comprises a housing 510 having a recess 530 suitable for receiving the filter cartridge and a first opening 550 to permit access to the filter content when a filter cartridge is inserted. The lid 570 engages with the housing by a sliding cooperation between protrusions on the housing and complementary recesses on the lid, and is retained in place by abutment against a sop plate and by a retaining clip. The storage unit also has a bottom 571 that engages with the housing in a manner analogous to that of the lid. A piston 600 is retained within the recess at a point beyond the first opening and defines a chamber 602 at the end of the recess distal from the recess opening. The housing has a second opening 603 into this chamber. The chamber 602 is suitable for receiving a fluid, for example, and not by way of limitation, a buffer for lysis of cells and preservation of nucleic acids and/or proteins, a fixative/preservative to prepare cells with the retention of the characteristic morphology (for cytological examination), a culture medium to sustain cell growth or an isotonic buffer suitable for the storage of biological material, or an appropriate buffer for the elution of the biological material from the filter. Accordingly, in some embodiments, the storage unit is provided with a suitable fluid of this type contained within the chamber. It will be appreciated that the fluid may be selected in accordance with the nature of the sample to be stored and the subsequent analysis required.

The piston 600 is retained within the recess but application of pressure, for example, by insertion of a filter cartridge, is able to push the piston further into the recess, reducing the size of the chamber and forcing the fluid therein into the remainder of the recess, and into contact with the filter and filter content. The filter cartridge 17 and storage unit 490 form a water tight seal around the filter, the filter content, and any surrounding liquid that may be present. It will be appreciated that varying the filter cartridge and storage unit dimensions and the provision and location of suitable 0-rings in order to achieve said water-tight seal will be apparent to the skilled person.

Assembly and Use

Assemblies of the invention may be provided as a kit directly to the user, who can then:

provide a sample into the collection chamber; assemble the device as described herein;

filter the sample using the device as described herein; remove the cartridge; and insert the filter portion into a storage unit as described herein for transportation to appropriate care giver or to an appropriate medical centre or testing facility.

It is an advantage that assemblies according to the present invention may be used in the home, with samples stored, optionally in a solution selected to facilitate storage and/or analysis of the captured material, and transported to a relevant care giver or to an appropriate medical centre or testing facility. Use of a storage unit according to the present invention permits samples captured on filters according to methods of the present invention to be sent hygienically and efficiently using, for example, regular national mail services. Patients thought to be at risk of developing, for example, bladder cancers, or those patients in remission from bladder cancer at present often have to undergo regular cystoscopy investigations, necessitating frequent hospital visits which may be inconvenient. Cystoscopy investigations are often uncomfortable and may carry a risk of complications. They are also expensive for the healthcare provider. The provision of a suitable device or kit for obtaining and processing samples at home which may be analysed without requiring the participation of the patient represents a significant improvement to patient wellbeing.

Accordingly, in some embodiments of the present invention, a kit is provided comprising a collection chamber as described herein and a filtration unit as described herein, and, optionally, instructions for using the assembly in a method as described herein. In some embodiments, the filtration unit is provided fully assembled. A sample is then provided, for example, through normal urination, into the collection chamber. The filtration unit is then fastened to the collection chamber. The user then flips the assembled device so that the collection chamber is now upside down at the top of the device, as shown in FIG. 3, and then provides manual pressure to force the liquid through the filter into the waste reservoir. The provision of one or more valves and/or backflow membranes allows pressure to equalise within the device. During the flow of the fluid through the filter, biological material, for example cells, is captured onto the filter. The quantity and type of material captured may be varied through the use of filters of different types (such as, and not by way of limitation, membrane filters or beads) or with different properties (such as, and not by way of limitation, varying pore size or coatings). After filtration, the filter cartridge with the filter content is removed and the remainder of the device may be discarded. In embodiments in which the filter cartridge is retained within a slot or recess, the user simply pulls the filter cartridge out of the remainder of the device. Kits of the invention may further comprise a storage unit as described herein. The user then inserts the filter cartridge into the storage unit as shown in, for example, FIG. 4 for convenient storage and transport. In some embodiments, the storage unit is provided as a lid and a base (denoted 57 and 51, respectively, in FIG. 1). In these embodiments, the filter cartridge is first inserted into the base 51. Lid 57 is then added, with the engagement of the lid with the base causing the seal to a chamber containing solution within the lid to break, thereby releasing the solution into contact with the filter content.

In some embodiments, the storage unit is provided as a single unit (denoted 490 in FIG. 4). This storage unit comprises a piston retained within the recess at a point beyond the first opening and defining a chamber at the end of the recess distal from the recess opening. The base of the storage unit has a second opening into this chamber. The chamber contains a solution, for example, and not by way of limitation, a buffer for lysis of cells and preservation of nucleic acids, a fixative/preservative to prepare cells with the retention of the characteristic morphology (for cytological examination), or a culture medium to sustain cell growth. Inserting the filter cartridge into the recess of the storage unit pushes the piston further into the recess, reducing the size of the chamber and forcing the liquid therein around the piston and into contact with the filter content where it may be retained during storage and transport.

The combined filter cartridge and storage unit may then be conveniently and hygienically transported to a testing/analysing facility or appropriate medical centre. Access to the filter content is facilitated by removal of the lid (denoted 57 or 570 in FIG. 1 or FIG. 4, respectively) to reveal the relevant opening in the storage unit housing. Filter content, for example, DNA, may be analysed using methods known in the art and methods described herein, with the presence or absence of certain known markers used to provide a diagnosis.

Alternatively, the assembly may be provided as a kit comprising a waste reservoir and filter support base that have not yet been fastened together. In these embodiments, the user must first assemble the filtration unit. It will be appreciated that filter cartridges and storage units, optionally comprising a solution housed within a chamber as described herein, may be provided separately to the remainder of the assembly as these may be selected specifically with regard to the intended application.

Suitable Filters

The present invention is based on the inventors' insight that devices comprising certain suitable filters may be utilised for capturing material from biological fluids for efficient analysis, for use in the diagnosis and monitoring of relevant conditions and diseases.

In some embodiments the assemblies and methods of the present invention may be used to capture cells from biological fluids. Previous studies have shown that it is possible to capture and separate cells from fluids using technical filtering (Wilding et al., 1998; Mohamed et al., 2004; Zheng et al., 2007; Lin et al., 2010). However, none of these methods provides the convenience and efficacy associated with the assemblies and methods of the present invention, that is, the provision of an assembly for the inexpensive and easy collection and processing of a sample which may be used by the patient or another caregiver to provide a sample of captured cells suitable for storing and sending through the post to a testing facility or appropriate medical centre.

Any filter material having the necessary character to capture material of interest may be used in assemblies and methods of the present invention. It will be appreciated that assemblies and methods of the present invention may be used for the capturing of different types of biological material from various biological fluids, for the detection, diagnosis and monitoring of a variety of diseases and conditions. Accordingly, it will be appreciated that the filter may be selected from filter media known in the art to have certain desirable characteristics, and in some cases it may be desirable to provide multiple filters in series. Where multiple filters are used, each filter may be identical to, or have different characteristics to, any other filter in the assembly.

For example, the capturing of cells of different sizes and different types may be achieved by use of a filter, or use of multiple filters, configured to exclude certain sizes or forms of cells, most likely by selection of filter pore size and or/pore arrangement. In some embodiments, it may be desirable to provide two or more filters in series, wherein a first filter captures large (e.g. human) cells and a second filter with smaller pores captures smaller cells (e.g. bacterial cells). Size exclusion may be achieved by use of particular pore or other aperture size, or by use of a particular pore form.

Filters may also be used that are made from materials, or have coatings, designed specifically to capture certain materials, for example, macromolecules such as proteins, DNA, RNA and metabolites.

The following examples of filter characteristics that may be suitable for use in some embodiments of the present invention are provided by way of illustration and are not intended to limit the invention to any particular filter type. These and other suitable filters are known in the art, and may be commercially available.

For capturing bacterial cells, a pore size of about 0.5 µm to 4 µm may be preferred. For capturing viral particles, viruses or bacteriophages a pore size of about 20 nm to 300 nm, more preferably of about 20 nm to about 50 nm may be used. For capturing blood components without platelets, a pore size of about 4 µm to 10 µm may be preferred. For capturing blood components without red blood cells, a pore size of about 7 µm co 12 µm may be preferred. For capturing tumour cells, a pore size of about 8 µm to 20 µm may be preferred, with about 8 µm to 12 µm being especially preferred, about 8 µm most preferred. For the capturing of macromolecules, ultrafiltration membrane filters with a specific molecular weight cut off limit (for example, but not by way of limitation, 50 kDa) selected to capture the macromolecules of interest may be used. Alternatively a capture agent, such as an antibody specific to a protein of interest or nucleic acid with a sequence that is complementary to that of interest, may be adhered to filter media (for example, but not by way of limitation, membrane filters, such as those made of nylon, Polyvinylidene difluoride or nitrocellulose, or chromatographic media such as sepharose or magnetic beads) allowing the macromolecule of Interest to be captured during filtration. The filter may be made of a suitable polymer material such as polycarbonate, nylon, or parylene, or a suitable non-polymer material such as silicone, as appropriate.

For some applications, membrane filters may be preferred, for example, in the capturing of cells from, for example, urine. The membrane filter may be a polycarbonate membrane, preferably a polycarbonate hydrophilic membrane, for example, a track-etched polycarbonate hydrophilic membrane. The filter may have a pore size of about 5-10 µm, preferably about 8 µm. Preferred membrane filters may include micromembrane filters such as commercially available polycarbonate filters, for example, Whatman Nuclepore track-etched polycarbonate hydrophilic filters, (diameter 25 mm, pore size 8 µm).

Suitable Solutions

In some embodiments the storage unit contains a solution selected to facilitate storage and/or analysis of the biological material. The solution may be, for example,
a buffer suitable for inducing cell lysis to permit analysis of nucleic acids or proteins released from the cell, a fixative/preservative to prepare cells with the retention of the characteristic morphology, a culture medium to sustain cell growth, an isotonic buffer suitable for storage of biological material, for example, phosphate buffered saline solution, or an appropriate buffer for the elution of the biological material from the filter. It will be appreciated that the solution will preferably be selected to correspond to the biological material to be captured and the analysis to be performed.

In some embodiments, assemblies of the invention could be used for the collection of exfoliated tumour cells from urine with the aim of analysing alterations in their DNA. For example, this may be using a polycarbonate membrane filter with a pore size of 8 µm to capture the tumour cells, then inserting the filter cartridge into the storage unit, and, optionally, releasing a cell-lysis and nucleic acid-preserving solution such as those commercially available from Qiagen or DNA Genotek [for example, as described in WO2003104251 A9] onto the filter content.

If the aim were to analyse the level of a particular protein within the tumour cells, the solution released onto the filter content may, for example, be a cell-lysis and protein-preserving solution such as RIPA buffer (commercially available from Millipore) or cell extraction buffer (commercially available from Invitrogen).

If the aim were to analyse the cells by cytology, the solution released onto the filter content may, for example, be a preservative buffer, for example one commercially available from Hologic (PreservCyt Solution, containing methanol) or a cellular growth medium, for example DMEM supplemented with 10% FBS, 1% L-glutamine, 100 U/ml penicillin and 100 µg/ml streptomycin.

In some embodiments and methods, assembles of the invention may be used for the collection of a particular cell-free protein from urine, for example, by using filter composed of Protein A/G coated sepharose beads to which an antibody which binds to the protein of interest has been attached, the filter cartridge then being placed into the storage unit and, optionally, an isotonic buffer such as phosphate buffered saline being released onto the filter content.

Uses of the Present Invention in Medical Detection, Diagnosis and Monitoring

Assemblies and methods for the collection of biological material from biological fluids, and the subsequent storage and optional processing of said biological material, as described herein, are of particular relevance for the detection, diagnosis and monitoring of diseases and conditions.

Whilst preferred embodiments are directed to the collection of cells from urine samples for the detection of genitourinary cancers, in particular, bladder cancer, it will be appreciated that through selection of an appropriate filter, device size, and, if present, fluid contained within a chamber in the storage unit, assemblies and methods as described herein may find utility in the detection, diagnosis and monitoring of a variety of diseases and conditions. For example, detection of hypermethylation of genes such as GSTP1, VHL, APC RASSF1A, Timp-3 in tumour cells from urine sediments is found in prostate and renal cancers (Cairns et al Nature Reviews Cancer 2007; 7:531-543). Also detection of changes in mitochondrial DNA may be useful in the early detection of cancers, monitoring of disease progression and response to therapy, and exfoliated tumour cells present in bodily fluid would be one source of mitochondrial DNA (Gabriel Dakubo Chapter 11 Mitochondrial DNA measurement in Exfoliated Cells for Cancer Detection and Monitoring: The copy Number Advantage in Mitochondrial Genetics and Cancer 2010 pp 259-274 ISBN: 978-3-642-11415-1 (Print) 978-3-642-11416-8 (Online)). Detection of elevated levels of MCM5 in urine sediments may be used to predict bladder cancer (Stober et al J Natl Cancer Inst 2002; 94:1071-9). Furthermore, RNA isolated from urine sediments has been analysed for diagnosis of acute rejection in kidney transplants, offering potential for the replacement of renal biopsies (Suthanthiran et al N. Engl. J. Med. 2013; 369:20-31).

Assemblies and methods of the invention may be used to capture free macromolecules (e.g. proteins, DNA, RNA or metabolites) in urine or other fluids. For example ovarian cancer patients have been shown to have altered levels of Glycosylated eosinophil-derived neurotoxin, COOH-terminal osteopontin fragments and the Q-subunit core fragment of human chorionic gonadotrophin, SMRP and Bcl-2 in their urine (Das and Bast Biomark Med. 2008; 2(3): 291-303). Detection of the S100A6 and S100A9 proteins in urine may have utility in the detection of upper GI tract cancers (Husi et al Proteornics Clin Appl. 2011; 5(5-6):289-99), whilst detection of the SAA4 and ProEGF proteins in urine may have utility in the detection of bladder cancer (Chen et al Journal of Proteomics 2013, 85: 28-43).

The assemblies and methods described herein may also be used for the collection and filtration of other biological fluids, such as saliva, sputum and blood, and bodily fluids obtained using more invasive methods such as, for example, pleural effusions, lavage fluid (for example ductal, bronchoalveolar) and sera for the analysis of captured material including via detection of genomic alterations associated with certain diseases and disorders including cancers such as lung and breast cancer (Belinsky et al Proc. Natl. Acad. Sci. USA, 95: 11891-11896, 1998; Ahrendt et al J. Natl. Cancer Inst., 91: 332-339, 1999; Evron et al Lancet, 357:1335-1336, 2001).

Filtration and concentration of blood may also be used in the isolation and analysis of circulating tumour cells (CTCs). Isolation and characterization of CTCs is a technical challenge as they make up only a small fraction of the total cells present in the blood. However, since CTCs reflect molecular features of cells within the tumour mass, they offer a potential way to diagnose or monitor progression/response of a patient in a relatively non-invasive way. CTCs have been identified in cancers such as in breast, prostate, lung, ovarian and colon cancer patients, where they have been shown to provide predictive and prognostic information. CTCs have also been identified in pancreatic patients, although no pivotal study using CTCs to guide clinical treatment has been undertaken (Cen et al Biochimica et Biophysica Acta 2012; 1826:350-356). The capture of circulating tumour cells from blood of patients with prostate, colorectal and breast cancer has been shown to be possible using a filtration method to take advantage of the increased size of tumour cells as compared to normal cells. Through appropriate filter selection, assemblies and methods described herein may also be applied to the capture and analysis of circulating cell-free DNA (cf-DNA).

Accordingly, methods described herein may involve the step of testing for markers known to be associated with a particular disease or condition. Said markers may be genetic markers, genomic alterations, the presence of or elevated/decreased levels of proteins (for example, antibodies), the presence of or elevated/decreased levels of bacteria or yeast, both as described herein and as documented in the art.

In some methods described herein, the marker may be a marker known to be associated with cancer. The cancer may be urinary, or gynecological cancer, for example, bladder cancer, prostate cancer, renal cancer, urethral cancer, ureteral cancer, urothelial cancer, urachal cancer, endometrial cancer, or ovarian cancer. The cancer may be a cancer associated with other organs, for example, liver cancer, melanoma, colorectal cancer, head and neck cancer, lung cancer, breast cancer, pancreatic cancer, or a cancer of the upper GI tract. The cancer may be a metastatic cancer. Markers associated with these and other cancers are known in the art. In some preferred embodiments, the marker is associated with a genitourinary cancer, preferably, bladder, prostate, or renal cancer. In some preferred embodiments, the marker is associated with bladder cancer, more preferably non-muscle invasive bladder cancer.

In some embodiments, the marker is associated with a condition other than cancer. For example, the marker may be associated with acute rejection in kidney transplants, which has the advantage of potentially obviating the need for invasive renal biopsies, or markers associated with bacterial and/or yeast infections, for example urinary tract infections such as cystitis and pyelonephritis.

It will also be appreciated that in some methods of the invention, the marker may not in itself be associated with a disease or condition but may instead be a genetic marker associated with an individual or particular parentage, for example, for use in forensic and paternity testing.

Analysis of Samples

It will be appreciated that the method used to analyze the filter content, and if present, the solution in which the filter having filter content has been stored, will depend upon the nature of the biological material and the purpose of the analysis. Methods for processing the material and/or solution and for detecting markers of interest are described herein and are known in the art.

Assemblies and methods described herein may be used in conjunction with UCyt+® and Urovysion® kits. A problem with these systems is the transportation of urine as well as the low number of cells and the low fraction of tumor cells in these samples. Proper preservation, cell isolation and increasing the fraction of tumor cells as provided by the assemblies and methods described herein may improve the use. In a recent study comparing FISH analysis (UroVysion) to cytology and cystoscopy as a follow-up method, Galvan et al (Cancer Cytopathol 2011; 119:395-403) noted that around 10% of samples could not be analysed due to too few urothelial cells in the sample or other technical reasons. Filtering with track-etched commercial filters has previously been used in conjuction with FISH analysis and improved the sensitivity of detection in the study compared to other studies done with conventional preparation methods (Meiers et al, Arch Pathol Lab Med 2007; 131:1574-1577). Meiers et al used a filter with 8 m pore size and found that it had an excellent yield for epithelial cell collection. The authors suggest that the increased sensitivity is partly due to the monolayer cell preparation created by filtering. However the present inventors believe that this may be attributed at least in part to the effect of increased tumor cell fraction in the sample. Meiers et al noted an adequacy rate of 95% with the filtering method compared to 85% by conventional methods, showing that robustness for FISH analysis is also improved by filtering, and may therefore be improved by use of assemblies and methods provided herein.

Particular Advantages of the Present Invention A key application of the invention is the diagnosis and surveillance of bladder cancer. The present invention was developed to provide a simple means for capturing bladder tumour cells from urine and storing/preserving DNA from these cells for later analysis. Important advantages include:

1) The cost of the assembly is low;
2) The assembly is simple to use, making it suitable for home use;
3) Immediate processing of the biological material after filtration through use of a storage unit containing a suitable solution to preserve and/or treat sample prior to analysis;
4) The fraction of tumour cells may be increased by size-based filtration, increasing the sensitivity of detection;
5) The filter content (e.g. captured cells) can be shipped by regular mail to an appropriate medical centre or testing facility, reducing the need for contact with the health care system;
6) Frequent and repeated sampling is unproblematic; and
7) Compared with cystoscopy, the use of the device for diagnosis and surveillance of bladder cancer will improve the quality of life for patients and dramatically decrease health care expenditure.

EXAMPLES

The following examples are set forth so as to provide those of ordinary skill in the art with a complete disclosure and description of how to practise the invention, and are not intended to limit the scope of the invention.

Capture of Cells on Micromembrane Filters

The following demonstrates the utility of membrane filters for the capturing of cells from urine for analysis.

Collection of samples Voided morning urine samples were collected from bladder cancer patients admitted for cystoscopy and transurethral resectioning (TURBT) at Herlev Hospital, Denmark and from healthy volunteers without known urological malignancies. Samples were sent to the Danish Cancer Research Center where they were processed within 4-6 hours after collection.

Processing of Urine Samples

For all patients and controls, 50 ml from each urine sample was sedimented by centrifugation, 2000×g for 10 min, the pellet was washed in PBS followed by another 10 min centrifugation. The supernatant was discarded and the pellet was resuspended in approximately 200 µl of PBS. In parallel, urine from the same sample was drawn into a disposable syringe and passed by positive force through a membrane filter mounted in a filter holder. Whatman Nuclepore track-etched polycarbonate hydrophilic filters were used, (diameter 25 mm, pore size 8 µm) and the corresponding filter holders. The sample was passed through the filter until saturation, with a maximum of 125 ml. The filter was rinsed with PBS before removal from the filter holder. Both urine sediment and the filter were stored at −80° C. until further processing.

For testing the functionality of the storage unit, the filter cartridge was transferred to the storage cassette, which was then mounted with the lid from an Oragene DNA Self-Collection Kit (disk format OG-250, DNA Genotek, Ottowa, Ontario, Canada).

DNA Isolation and Bisulfite Conversion

DNA was isolated from urine sediment and filter by QiaAmp DNA Mini Kit (Qiagen GmbH, Hilden, Germany). Filter samples and urine sediments were incubated with ATL buffer and proteinase K at 56° C. for at least 1 hour (filter) or overnight (sediments) Subsequent processing was done according to manufacturer's instructions. DNA from filters and sediments were eluted in 50 µl and 100 µl of buffer AE, respectively, and stored at −80° C. DNA concentration was measured using a NanoDrop 1000 spectrometer. The samples from 16 patients and 9 healthy controls did not contain sufficient DNA for analysis and were discarded.

Bisulfite conversion was done using the EZ DNA Methylation-Gold Kit (Zymo Research) according to the manufacturer's protocol. The bisulfite-treated DNA was eluted in 20 µl of M-Elution Buffer and stored at −80° C. For paired samples (sediment and filter sample) the same amount of DNA was used, with a maximum of 500 ng. In cases where the DNA concentration was too low to be accurately determined using the NanoDrop spectrometer, the maximum sample volume (20 µl) was used for bisulfite treatment. Semi-quantitative analysis of the promoter CpG islands of BCL2, CCNA1, EOMMES, HOXA9, POU4F2, SALL3 and VIM2 was performed using TaqMan-based real-time PCR (MethyLight) assays, using previously described primers, probes and conditions [12]. Reactions were performed on the LightCycler 480 platform using the LightCycler 480 Probes Master Kit (Roche, Mannheim, Germany) and 1 µl of bisulfite-treated DNA per reaction. In vitro methylated DNA (IVM; CpGenome™ Universal Methylated DNA, Chemicon/Millipore, Billerica, Mass.) and whole-genome amplified DNA served as positive and negative controls for methylation, respectively. Methylation levels were calculated as percent methylated reference (PMR; Ref. [Weisenberger D J, Campan M, Long T I, Kim M, Woods C et al. (2005). Nucleic Acids Res 33: 6823-6836]) by normalizing marker-specific reaction values to ALUC4 values relative to the same values for fully methylated control (IVM). Samples with a concentration below the equivalent of 0.25 ng/µl non bisulfite-treated DNA were excluded. Cut-off PMR values for HOXA9, POU4F2, SALL] and VIM2 were 3, 2, 0.5 and 2, respectively. BCL2, CCNA1 and EOMES showed no background methylation in DNA isolated from urine filter and sediment samples from healthy controls.

Real Time Quantitative Methylation-Specific Polymerase Chain Reaction (MethyLight)

Methylation analysis was performed using MethyLight, a quantitative fluorescence-based, real-time PCR assay (Eads ⇔ al., 2000, Nucleic Acids Res. 28, E32). Primers and probes were designed for 7 gene promoter CpG islands and for ALUC4, which was used to control for the amount of input DNA (Weisenberger et al., 2005, Nucleic Acids Res. 33, 6823-6836). Bisulfite-converted, in vitro-methylated DNA (IVM; CpGenomem Universal Methylated DNA, Chemicon) was analyzed to normalize for any amplification bias between a target gene and ALUC4. Reactions were performed on the Roche LightCycler@ 480 Real-time PCR system using the Lightcycler: 480 Probes Master Kit (Roche).

Cell Culture and Model System

The human ureter transitional cell carcinoma cell line 639V was purchased from DSMZ (Braunschweig, Germany). Cells were maintained in DMEM medium supplemented with 10% fetal bovine serum at 37° C. in a humidified incubator with 5% $CO_2$. Lymphocytes from a healthy donor were prepared from peripheral blood according to a previously described protocol [Thurner B, Roder C, Dieckmann D, Heuer M, Kruse M et al. (1999) J Immunol Methods 223: 1-15] and stored at −80° C. until use. Cells in suspension were counted and their diameter was measured using a Countess Automated Cell Counter (Invitrogen, Carlsbad, Calif., USA). Lymphocytes and 639V cells were mixed in different ratios in 100 ml of PBS and processed using the filtration device.

Mutation Analysis

Detection and quantification of FGFR3 mutations (R248C, S249C, G370C and Y373C) and corresponding wildtype sequences were performed by droplet digital PCR (ddPCR), using the QX200 system (Bio-Rad Laboratories, Hercules, Calif.) and hydrolysis probe-based assays (PrimePCR ddPCR Mutation Detection Assays; Bio-Rad). The PCR mixture contained 11 µl of ddPCR droplet supermix for probes (no dUTPs), 1.1 µl of mutation primer/probe mix (FAM), 1.1 µl of wildtype primer/probe mix (HEX) and 2 µl of DNA in a final volume of 22 µL. Twenty microliters of this mixture and 70 µl of droplet generation oil were transferred to different wells of a droplet generation cartridge. After formation of droplets using the droplet generator, samples were transferred to a 96-well PCR plate and subjected to amplification for 40 cycles at 94° C. for 30 sec. and 55° C. for 60 sec. Droplets (on average ~16,000 per reaction) were analyzed on the droplet reader, and Quantasoft software (version 1.4.0.99) was used for analyzing DNA concentrations. Cutoff settings were determined using mutation-positive and -negative control DNA samples.

Figure 5:
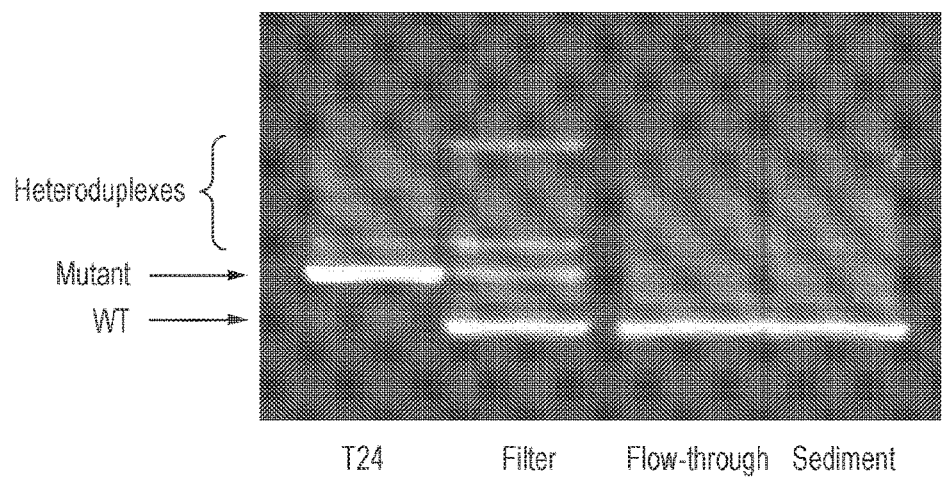
FIG. 5 shows denaturing gradient gel electrophoresis (DGGE) analysis of HRAS exon 2. The human cell line T24 is homozygous for the G12V mutation.

The inventors first used cultured cells to test 1) if it was possible to capture cells on a commercial micromembrane filter and 2) if low-abundant bladder tumour cells could be enriched. Purified, cultured human lymphocytes diluted in PBS were spiked with 0.5% bladder cancer cells (the human cell line T24). Half of the volume of the cell mixture was sedimented by centrifugation, and the remaining half was passed through a filter. The flowthrough from the filter was also collected and sedimented by centrifugation. DNA was isolated from the unfiltered, filter and flowthrough samples and analysed for the HRAS G12V mutation previously established to be present in the cell line T24. PCR in combination with denaturing gradient gel electrophoresis (DGGE) was used to resolve mutant and wildtype HRAS. As shown in FIG. 5, the filtered sample was clearly positive for the HRAS G12V mutation, whereas the unfiltered and flowthrough samples were negative (DGGE has a detection level at around 2-3% mutated allele on a wild-type background). These results show that tumour cells are retained on the filter but also indicate that the fraction of tumour cells is increased in the filter compared to the unfiltered sample.

Figure 6:
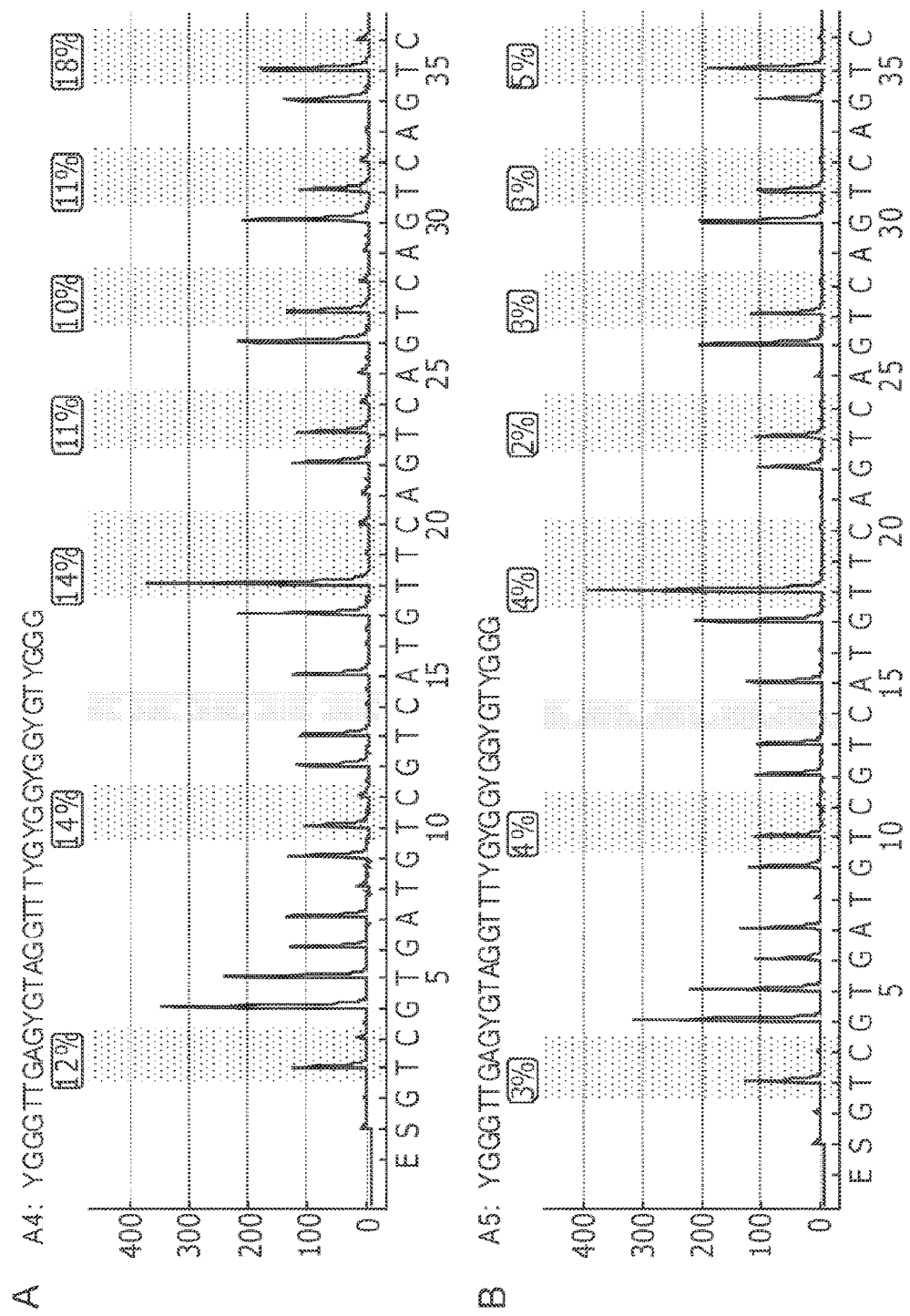
FIG. 6 shows pyrosequencing analysis of 6 CpG sites in the BCL2 promoter. A) Filtered sample, B) unfiltered sample.

The same DNA samples were also analyzed for DNA methylation levels in the promoter region of BCL2, which is fully methylated in T24 cells and unmethylated in normal lymphocytes. As shown in FIG. 6, the unfiltered and flowthrough samples showed an average methylation level of 3-4%, similar to the level in normal lymphocytes. In contrast, the filter sample shows an average methylation level of 13%. This analysis confirmed that the fraction of tumour cells is increased in the filter.

Figure 7:
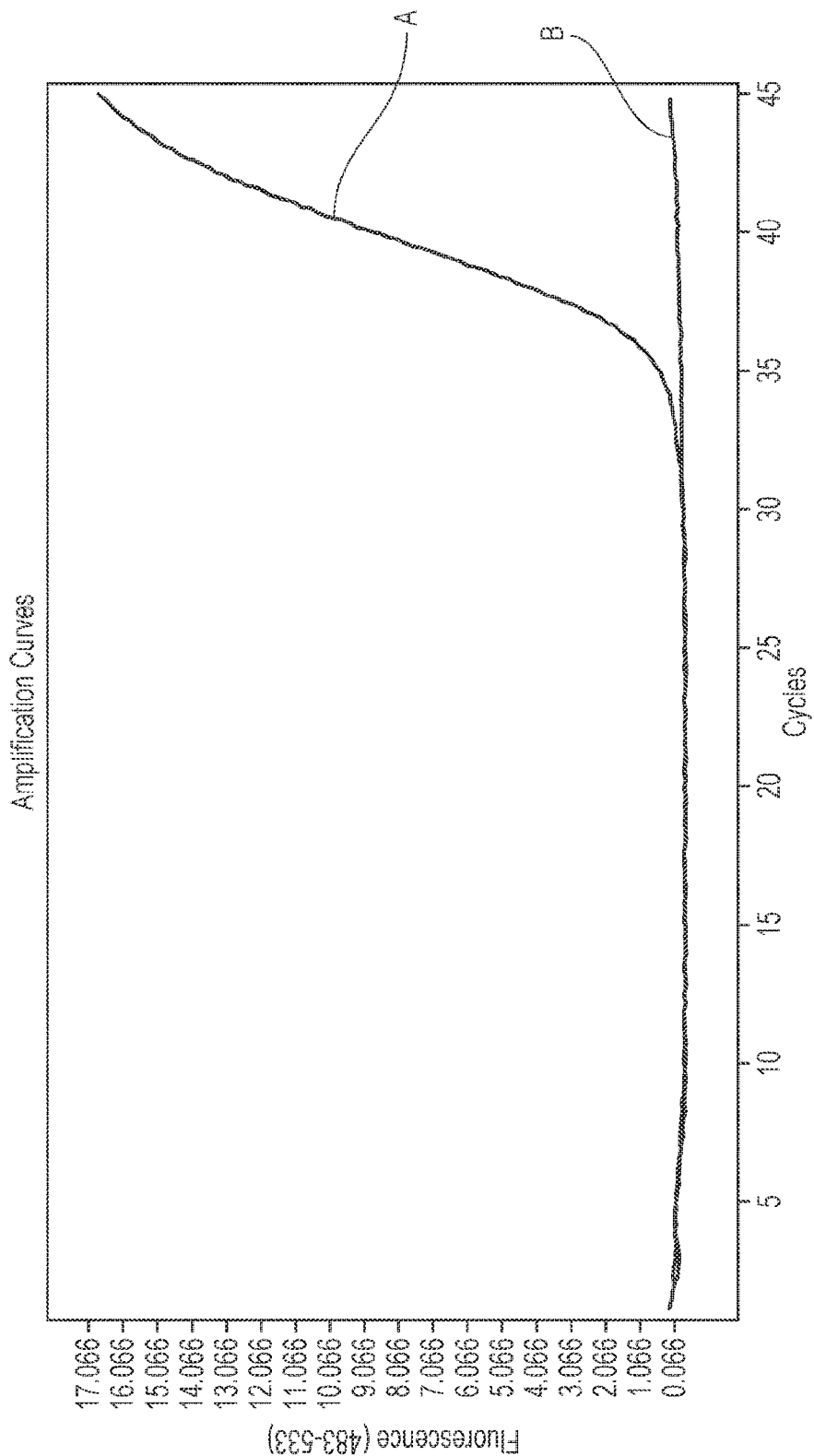
FIG. 7 shows MethyLight analysis of the BCL2 promoter in urine samples from pt. X (diagnosed with a high-grade Ta tumour). A positive signal was obtained only for the filter sample; A labels the "Filter", B labels the "Sediment".

Next, urine samples from 204 bladder tumour patients and 29 healthy controls were examined in a split-sample design: For all patients and controls, urine samples were subjected in parallel to sedimentation (50 ml) and filtration (until saturation of filter or max. 125 ml). DNA was isolated, treated with sodium bisulfite and tested for 7 methylation markers (CCNA1, BCL2, EOMES, POU4F2, SALL3, HOXA9 and VIM2) using real-time MethyLight assays. All of these markers have been reported in literature to be aberrantly hypermethylated in bladder cancer. A cut-off value for background methylation was established by analysis of samples from 10 of the healthy controls. FIG. 7 gives an example of parallel analysis of filtered and sedimented components of the same urine sample from a bladder tumour patient.

Overall, the sensitivity was 81 when urine sediments from the 204 bladder tumour patients were analyzed for the seven DNA methylation markers, while it was 87% for the corresponding filter samples able 1). Of note, for low-grade Ta tumours that are difficult to detect on the basis of urine analysis, the sensitivity increased from 75% in sediments to 84% in filter samples.

TABLE 1

Sensitivity of seven DNA methylation markers in filtered and sedimented urine samples from bladder tumour patients (N = 204).

| Pathology | Sediment | Filter |
|---|---|---|
| Low grade Ta/dysplasia | 74/98 (75%) | 82/98 (84%) |
| High grade Ta | 24/31 (77%) | 25/31 (81%) |
| T1 | 27/30 (90%) | 28/30 (93%) |
| >T2 | 17/19 (89%) | 18/19 (95%) |
| CIS | 24/26 (92%) | 25/26 (96%) |
| Total | 166/204 (81%) | 178/204 (87%) |

Figure 8:
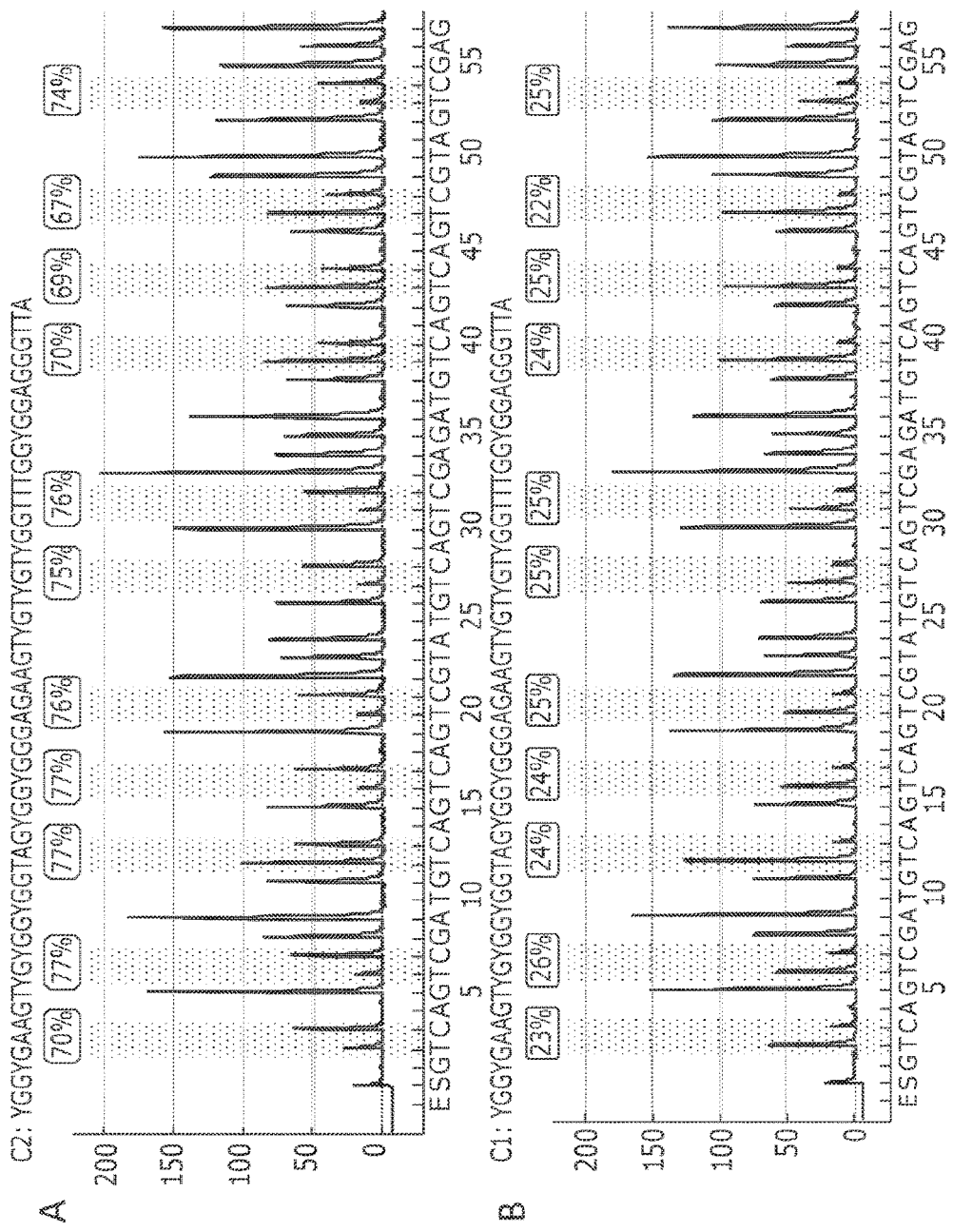
FIG. 8 shows pyrosequencing analysis of the BCL2 promoter. A) Filtered sample from pt. Y, B) sediment from pt. Y.

In the majority of samples analysed, the fraction of tumour DNA was larger in the filter than in the corresponding sediment Some of these results were confirmed by pyrosequencing (FIG. 8).

The majority of the 26 tumours that were negative for all seven markers were NMIBC, including one carcinoma in situ (CIS), 22 Ta tumours, and two T1 tumours. Among the 19 controls, three were positive (two in both filter and sediment; one in filter only) One of these had been misclassified and had a bladder tumour. The second had prior problems with the bladder, and subsequent cystoscopy showed the presence of a hyperplastic lesion. The third was negative on cystoscopy.

In conclusion, the present inventors have shown that using micromembrane filters (for examples, commercial polycarbonate membrane filters), it is possible to capture cells from urine samples and isolate DNA for subsequent methylation analysis. Accordingly, in some embodiments, the present invention relates to a method of passing a biological fluid simple, such As a urine sample, through a micromembrane filter. In general, the fraction of tumour DNA was larger in the filter than in the corresponding sediment. For 87% of the bladder tumour patients, the filter sample was positive for tumour-specific DNA methylation markers. The corresponding urine sediments were positive in 81% of the cases.

Capture of Cells Using a Device According to the Present Invention and Subsequent Analysis As described above, the inventors have shown that cells in urine samples can be captured on micromembrane filters using a syringe and a commercial filter holder. The following non-limiting example details use of a collection and filtration device comprising such a membrane according the present invention. A technical drawing of the collection and filtration device used is shown in FIG. 1 (described above).

Morning urine samples were collected from 30 patients admitted for bladder cystoscopy at Herlev Hospital. The samples were processed within 3-6 hours at the Danish Cancer Research Center. The sample volume varied between 150 and 400 ml, average 240 ml (Table 2). The filtration devices were mounted with an 8 μm pore size, track-etched polycarbonate filter (Whatman). After filtration, the filters were removed from the filtration device and stored at −80° C. until further processing.

DNA was isolated from the filters as described in above. DNA was eluted in 50 μl of AE buffer and stored at −80° C. Bisulfite conversion of DNA was performed as described above. The DNA concentration was determined by quantitative PCR analysis of GAPDH. The methylation status of seven methylation markers (CCNA1, BCL2, EOMES, POU4F2, SALL], HOXA9 and VIM2) was determined using MethyLight assays, as described above. The average DNA yield for the 30 urine samples was 242 ng (range 6 to 1,000 ng; Table 2).

TABLE 2

DNA yield from 30 urine samples, processed using the urine filtration device. The DNA concentration was determined by qPCR (*estimated figure, measure out of range).

| Patient ID | Pathology | Processed volume (ml) | DNA, yield (ng) |
|---|---|---|---|
| 1 | T2, high grade | 250 | 661 |
| 2 | Ta, low grade | 150 | 16* |
| 3 | Inflammation | 300 | 1060 |
| 4 | Ta, low grade | 250 | 321 |
| 5 | Normal bladder | 450 | 121 |
| 6 | Normal bladder | 300 | 10.1* |
| 7 | Glandular metaplasia/normal | 300 | 331 |
| 8 | Ta, low grade | 250 | 388 |
| 9 | Ta, low grade | 200 | 202 |
| 10 | Ta, low grade | 150 | 160 |
| 11 | Ta, low grade | 350 | 23 |
| 12 | Ta, high grade | 250 | 6.3* |
| 13 | Normal bladder | 150 | 397 |
| 14 | Normal bladder | 450 | 26.4 |
| 15 | Inflammation | 300 | 700 |
| 16 | Ta, high grade | 350 | 72 |
| 17 | Ta, high grade | 300 | 520 |
| 18 | Ta, low grade | 150 | 517 |
| 19 | Ta, low grade | 150 | 8.7* |
| 20 | Ta, high grade | 150 | 59 |
| 21 | Tis | 150 | 45.2 |
| 22 | Ta, low grade | 450 | 145 |
| 23 | N.A | 150 | 181 |
| 24 | Ta, high grade | 150 | 303 |
| 25 | T1 and Tis | 200 | 12.9* |
| 26 | T2, high grade | 150 | 40.4 |
| 27 | Ta, low grade | 250 | 79 |
| 28 | Ta, low grade | 150 | 19.5* |
| 29 | Normal bladder | 150 | 283 |
| 30 | Inflammation | 300 | 549 |
| Average | | 240 | 242 |

Of the 30 cases included in this analysis, 20 were diagnosed with a bladder tumour upon cystoscopy (Table 2). For two of these tumour cases, the DNA yield was too low for methylation analysis. The 18 remaining samples were tested for the seven bladder cancer-associated methylation markers (Table 3). Sixteen of these samples were positive for one or more markers, corresponding to a diagnostic sensitivity of 89%.

This figure is encouraging as the majority of the patients in this cohort presented with small noninvasive tumors, which are notoriously difficult to detect in urine.

TABLE 3

MethyLight analysis of seven DNA methylation markers in urine DNA from 18 bladder tumour patients. The pathology of these cases is indicated in Table 2.

| Patient Id | BCL2 | CCNA1 | EOMES | HOXA9 | POU4F2 | SALL3 | VIM2 | POSITIVE MARKERS | SCORE |
|---|---|---|---|---|---|---|---|---|---|
| 1 | + | + | + | + | − | + | + | 6/7 | Positive |
| 2 | − | − | − | + | − | − | + | 2/7 | Positive |
| 4 | − | − | − | − | − | − | − | 0/7 | Negative |
| 8 | + | + | − | − | + | + | + | 5/7 | Positive |
| 9 | − | + | + | + | − | − | − | 3/7 | Positive |
| 10 | + | − | + | + | + | + | + | 6/7 | Positive |
| 11 | − | − | − | − | − | − | + | 1/7 | Positive |
| 12 | + | + | + | + | + | + | + | 7/7 | Positive |
| 16 | − | + | − | − | − | − | − | 1/7 | Positive |
| 17 | − | + | − | + | − | − | + | 3/7 | Positive |
| 18 | − | − | − | − | − | − | − | 0/7 | Negative |
| 20 | + | + | − | + | − | + | + | 5/7 | Positive |
| 21 | + | + | − | + | + | + | + | 6/7 | Positive |
| 22 | − | + | − | + | − | − | − | 2/7 | Positive |
| 24 | + | + | + | − | − | + | + | 5/7 | Positive |
| 25 | + | + | − | + | + | + | + | 6/7 | Positive |

TABLE 3-continued

MethyLight analysis of seven DNA methylation markers in urine DNA from 18 bladder tumour patients. The pathology of these cases is indicated in Table 2.

| Patient Id | BCL2 | CCNA1 | EOMES | HOXA9 | POU4F2 | SALL3 | VIM2 | POSITIVE MARKERS | SCORE |
|---|---|---|---|---|---|---|---|---|---|
| 26 | + | + | − | + | + | + | + | 6/7 | Positive |
| 27 | + | − | − | + | − | − | + | 3/7 | Positive |
| Total positive | | | | | | | | | 16/18 (89%) |

Evaluation of Device Performance

Figure 9:
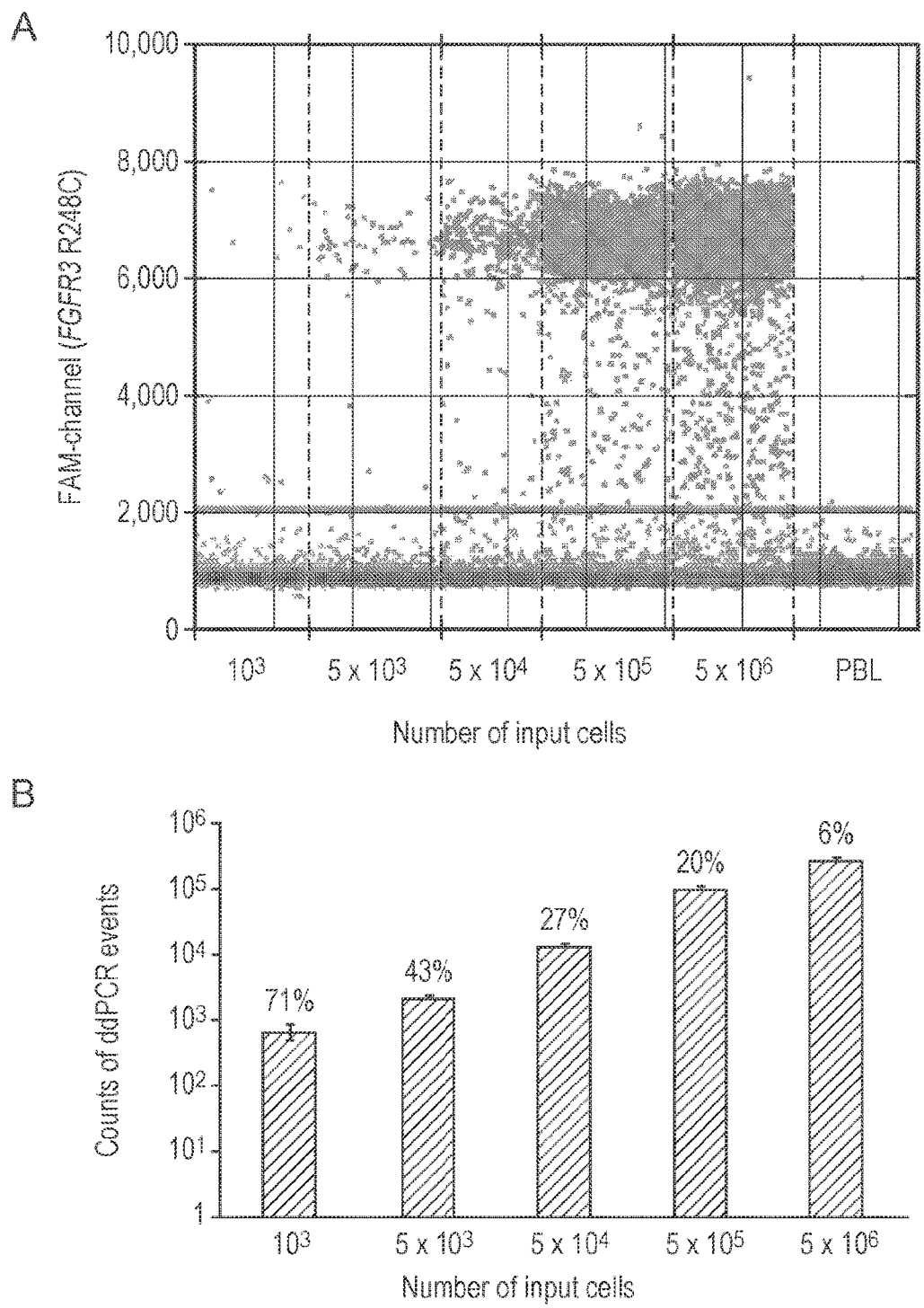
FIG. 9 shows capture of tumor cells from fluid by filtration using a device mounted with an 8-μm pore size polycarbonate membrane filter. Data of triplicate measurements (each on 4% of total DNA) from one experiment are represented as means±SD. Percentages above bars represent the number of recovered cells relative to the number of input cells.

As a model system to evaluate the ability of the device to capture and enumerate tumor cells from fluid samples, the inventors used 639V bladder cancer cells, which have a point mutation (p.R248C; c.742C>T) in the gene encoding fibroblast growth factor receptor 3 (FGFR3) with loss of the corresponding wildtype allele. In the first set of experiments, 100 ml of PBS containing between $10^3$ and $5 \times 10^6$ 639V cells was added to the collection chamber of the device and forced through a polycarbonate membrane filter with a pore size of 8 µm. To quantify the number of 639V cells captured on the filter, total DNA was extracted and determined the number of mutant FGFR3 molecules using a droplet digital PCR (ddPCR) assay. In this setting, one positive event is equivalent to one cell. Positive signals were reproducibly obtained for all samples when 2 µl (4%) of the extracted DNA was used as template for ddPCR (FIG. 9A) Notably, for the lowest concentration of cells ($10^0$ in 100 mL), the average number of signals obtained per 2 µl-sample reaction was 28, equivalent to an overall recovery of 70% of the input cells (FIG. 9B).

The 30% loss of input material may at least in part be ascribed to an expected loss of DNA during extraction. At higher concentrations of cells, there was a decrease in recovery rate, down to 5% at $5 \times 10^6$ cells/100 ml. This lower recovery was expected as saturation of the filter will cause release of the pressure valve and a direct flow of the remaining fluid and its cellular content into the waste reservoir. This initial testing suggested that the filtration device can be used to effectively capture bladder cancer cells from a fluid, and that the recovery rate is particularly high at low concentrations of cells where the capacity of the filter has not yet been reached.

Figure 10:
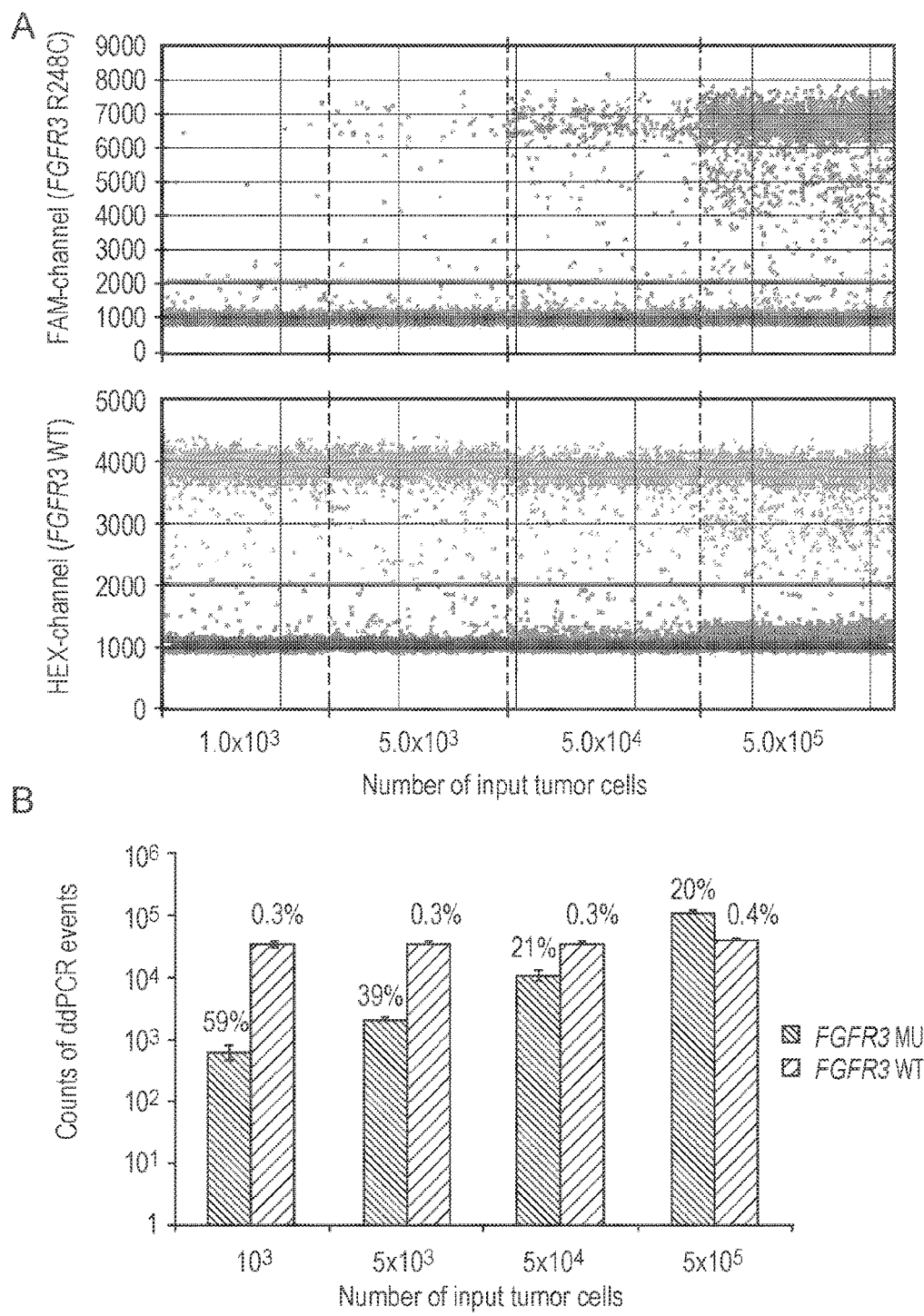
FIG. 10 shows filtration-based enrichment of bladder cancer cells in a background of normal lymphocytes. A) ddPCR fluorescence amplitude plots of FGFR3 R248C-FAM probe fluorescence signal (upper panel) and FGFR3 WT-HEX probe fluorescence signal (lower panel). B) Bar chart showing the number of mutant and WT FGFR molecules relative to number of input tumor cells. Total counts of FGFR molecules were calculated on the basis of three independent ddPCR tests, each using 4% of total DNA as template, and are represented as means±SD. Percentages above the bars represent the number of recovered cells relative to the number of input cells.

To test the ability of the filtration device to enrich for bladder cancer cells present at low abundance in a background of normal cells, the inventors spiked between $10^3$ and $5 \times 10^5$ 639V bladder cancer cells into 100 ml of PBS containing $10^7$ normal purified cultured human lymphocytes (diameter 7-8 µm) and processed the suspension using the filtration device. Analysis of DNA extracted from filters by ddPCR showed signals for both mutant (R248C) and wild-type FGFR3 (FIG. 10A). Vertical lines represent manually set cutoff settings. DNA was extracted from the filters and tested for mutant FGFR3 (R248C) molecules using ddPCR. DNA from normal peripheral blood lymphocytes (PEL) was used as a control for wildtype FGFR. The results shown are from one of two independent experiments. Most important, the recovery rate of mutant DNA was similar to that achieved with pure solutions of 639V bladder cancer cells (FIG. 10B). Although the processing of samples by filtration eliminated the majority of blood lymphocytes (>994), there was a consistent background of wildtype FGFR3 alleles (FIG. 10A, B). These background cells may represent residual monocytes, which are larger than the pore diameter of the filter, and thrombocytes, which are smaller but tend to form aggregates and therefore may also be captured on the filter.

This demonstrates that the device is capable of isolating low abundant tumour cells, and therefore may therefore be useful for diagnosing smaller less aggressive tumours earlier. The size and stage of the tumour is normally reflected by the number of cells expected in a urine sample. The smaller less aggressive tumours would not shed as many cells into the urine as a more established tumour and therefore could potentially be missed on standard diagnostic techniques. This also demonstrates that DNA can be isolated from tumour cells spiked into PBS containing normal peripheral blood lymphocytes, showing that the device can isolate tumour cells from normal blood cells.

Detection of Bladder Cancer in Urine Specimens

Figure 11:
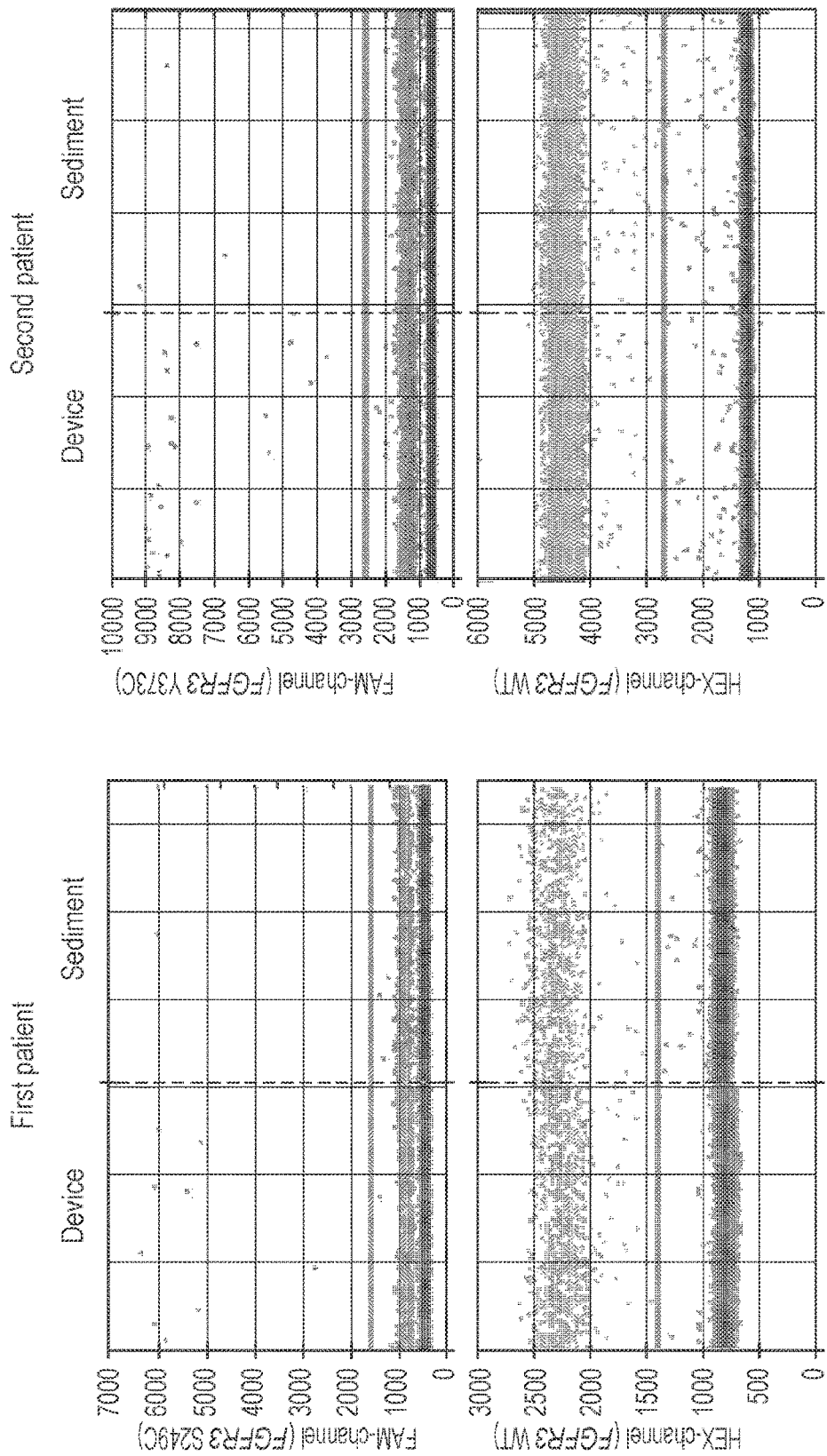
FIG. 11 shows detection of tumor-derived DNA in paired urine samples prepared by device filtration and sedimentation. Equimolar amounts of DNA from filters and sediments were tested for FGFR3 mutations using ddPCR.

Having demonstrated that cultured bladder cancer cells spiked into purified lymphocytes can be captured and enriched using the filtration device, the inventors next tested the same approach on urine samples from patients with bladder tumors. In order to test whether filtration could increase the sensitivity over conventional sediment analysis by increasing the ratio of normal-to-tumor cells, they first tested 13 urine samples in a split-sample setup, where one part of each sample was processed by filtration and the remainder was sedimented by centrifugation. DNA isolated from all filter and sediment samples were screened for four common FGFR3 mutations (R248C, S249C, G370C and Y373C) using ddPCR. Eight of the samples (58%) were positive for one of these mutations (Table 4). Quantitative analysis showed that the ratio of mutant-to-wildtype DNA was higher in the filtered samples than in the corresponding sediments (Table 4). Most important, the greatest enrichments (6.5 and 8.0 times, respectively) were achieved for the two samples representing the lowest mutant-to-wildtype ratios (FIG. 11)

TABLE 4

Fractions of mutant (Mut) and wildtype (WT) FGFR3 in urinary cells collected by device filtration or sedimentation.

| Patient ID | FGFR3 mutation | Mut/WT ± SE | | Device/ Sediment |
|---|---|---|---|---|
| | | Device | Sediment | |
| 106 | S249C | 0.848 ± 0.047 | 0.812 ± 0.014 | 1.05 |
| 107 | S249C | 0.729 ± 0.015 | 0.396 ± 0.004 | 1.84 |
| 110 | Y373C | 0.182 ± 0.001 | 0.096 ± 0.003 | 1.89 |
| 119 | Y373C | 0.008 ± 0.002 | 0.001 ± 0.000 | 7.92 |
| 120 | S249C | 0.041 ± 0.002 | 0.034 ± 0.002 | 1.19 |
| 121 | S249C | 0.006 ± 0.001 | 0.001 ± 0.000 | 6.47 |
| 126 | S249C | 0.022 ± 0.005 | 0.020 ± 0.004 | 1.09 |
| 127 | Y373C | 0.011 ± 0.001 | 0.004 ± 0.000 | 2.82 |

SUMMARY

Cells shed into the urine provide a convenient source for noninvasive detection of bladder cancer. Collection of cells and downstream testing by cytology or analysis of tumor-specific markers may offer an alternative or adjunct to cystoscopy in bladder cancer diagnosis and surveillance. However, the practical use of urine-based tests is often limited by inconvenience of sample handling, difficulties in analyzing large sample volumes, the need for rapid sample processing to avoid degradation of the cellular content, and insufficient analytical sensitivity due to a low ratio of tumor-to-normal cells. Described herein is a filtration device, designed for home or point-of-care use, which enables collection, enrichment and immediate preservation or treatment of tumor cells from urine. In spiking experiments, the use of this device in combination with droplet digital PCR for DNA-biomarker quantification provided efficient recovery of bladder cancer cells with elimination of >99% of excess lymphocytes. The performance of the device was further evaluated by DNA-based analysis of cells collected from urine from patients with bladder cancer, including some with low-grade Ta tumors. The ratio of tumor-to-normal DNA was higher in filtered samples compared with the same samples processed by sedimentation and showed high sensitivity. The ability to easily collect, process and ship diagnostic cells from urine may broaden the use of noninvasive tests for detection and follow-up of bladder cancer.

REFERENCES

All publications, patent and patent applications cited herein or filed with this application, including references filed as part of an Information Disclosure Statement are incorporated by reference in their entirety.
US-2009.0306610-A1 Van Den Heuvel et al.
US-2016/0223442-A1 Goldberg et al
U.S. Pat. No. 4,829,005-A Friedman et al.
U.S. Pat. No. 5,139,031-A Guirguis
U.S. Pat. No. 5,224,489-A Guirguis
U.S. Pat. No. 5,471,994-A Guirgllis
U.S. Pat. No. 5,484,572-A Katakura et al
U.S. Pat. No. 5,846,487 Bennett, II
U.S. Pat. No. 5,849,505-A Guirgills
U.S. Pat. No. 6,176,836 Trudil et al
U.S. Pat. No. 6,733,250 Yajima.
U.S. Pat. No. 7,846,393 Tai et al.
U.S. Pat. No. 7,846,743 Tai et al.
U.S. Pat. No. 8,288,170 Tai et al.
GB-1311457-A Panoz, D E
WO-20061116327-A1 California Inst Of Techn
WO-2010/31140A1 Diagcor Bioscience foe Ltd
WO-2013/022974-A1 The Henry M. Jackson Foundation for the Advancement of Military Medicine, Inc.
WO-2014/081877A1 Univ Columbia
Birkhahn, M et al., A Novel Precision-Engineered Microfiltration Device for Capt. me and. Characterization of Bladder Cancer Cells in Urine, European Journal of Cancer (2013).
Bostwick, I. et al, Improved Filter Method for Urine Sediment Detection of Urothelial Carcinoma by Fluorescence In Situ Hybridization, Arch. Pathol. Lab. Med., 131: 1574-1577 (2007).
Villicana, P. et al., Urine-Based Assays for the Detection of Bladder Cancer, Biomark Med., 3(3): 265 (2009).

The invention claimed is:
1. A biological fluid filtration assembly comprising a filtration device for filtering a biological fluid sample, the filtration device comprising:
A collection chamber (1) having a longitudinal axis,
a waste reservoir (21),
a filter support platform (15),
a removable filter cartridge (17),
wherein the removable filter cartridge (17) houses a filter that is characterized such that when the biological fluid sample is present in the filtration device, the filter will capture a target biological material present in the biological fluid sample; wherein the filter support platform (15) is removably connected to the collection chamber (1) and to the waste reservoir (21) such that the filter support platform (15) separates the collection chamber (1) and the waste reservoir (21) such that they permit passage of a biological fluid from the collection chamber (1) along the longitudinal axis into the waste reservoir (21) through the filter of the removable filter cartridge (17) when the biological fluid sample is present in the filtration device; and
wherein the filter support platform (15) is arranged and configured such that it slidably retains the removable filter cartridge (17), and wherein the filter support platform (15) comprises a slotted recess (25), wherein the removable filter cartridge (17) is insertable into and removable from the slotted recess (25) in a sliding movement, wherein the sliding movement is perpendicular to the longitudinal axis, and
a storage unit (49) having a body comprising a recess (53) for slidably receiving and engaging with the removable filter cartridge (17), wherein the body is arranged and configured such that, when engaged, the filter of the removable filter cartridge (17) is sealed within the body of the storage unit (49).
2. The assembly of claim 1, wherein the storage unit body has an opening (55) to permit access to the filter and/or filter content of the filter and/or a liquid surrounding the filter when the removable filter cartridge (17) is in place, and wherein the storage unit (49) further comprises a removable lid covering the opening (57).
3. The assembly of claim 1, wherein the storage unit comprises a solution chamber containing a solution selected to facilitate storage and/or analysis of the biological material, and wherein engagement of the removable filter cartridge (17) with the storage unit (49) causes the release of the solution into contact with the filter.
4. The assembly of claim 1, wherein the storage unit (490) has a piston (600) retained within the recess (530), the piston and recess defining a solution chamber distal from the recess opening, the solution chamber (602) containing a solution selected to facilitate storage, processing and/or analysis of the biological material, the piston being configured such that insertion of the removable filter cartridge (17) into the recess causes the piston to move further in to the recess, such that the solution contained within the chamber is forced around the piston into contact with the filter.
5. The assembly of claim 2, wherein the lid (57) has a solution chamber containing a solution selected to facilitate storage and/or analysis of the biological material, and wherein engagement of the lid with the storage unit (49) body causes the solution to be released such that it contacts the filter.
6. The assembly of claim 3, wherein the solution selected to facilitate storage and/or analysis of the biological material is:

(i) a buffer suitable for inducing cell lysis to permit analysis of nucleic acids, proteins, or other macromolecules released from the cell;
(ii) a fixative/preservative to preserve cells with the retention of the characteristic morphology;
(iii) a culture medium to sustain cell growth; and/or
(iv) an isotonic buffer suitable for storage of biological material.

7. The assembly of claim 1, wherein filtration device has means for application of pressure to a fluid contained within the collection chamber when the device is assembled to force the fluid through the filter into the waste reservoir (21).

8. The assembly of claim 1, wherein the collection chamber (1) is compressible such that when the filtration device is assembled and the collection chamber (1) contains a fluid sample, compression of the collection chamber (1) applies pressure to the fluid, thereby forcing the fluid through the filter into the waste reservoir (21).

9. The assembly of claim 8, wherein the collection chamber (1) is a cylindrical bag (3), and wherein a spring (5) surrounds the cylindrical bag along its cylindrical axis, permitting compression of the cylindrical bag in the direction of its cylindrical axis.

10. The assembly of claim 8, wherein the filter support platform (15) comprises a valve (37) to allow pressure within the device to equilibrate during and after application of pressure.

11. The assembly of claim 1, wherein the biological fluid is urine or a bladder wash, or blood or serum.

12. The assembly of claim 1, wherein the biological material is cells suspended in the biological fluid.

13. The assembly of claim 1, wherein the filter is a membrane filter.

14. The assembly of claim 13, wherein the filter is a polycarbonate membrane.

15. A method of capturing biological material from a biological sample using an assembly according to claim 1, the method comprising:
(i) providing a biological fluid sample into the collection chamber;
(ii) connecting the collection chamber to the filter support platform and waste reservoir;
(iii) causing the biological fluid sample to flow from the collection chamber into the waste reservoir through the filter to capture biological material present in the fluid; and
(iv) removing the filter cartridge from the filter support platform and inserting the filter cartridge into the storage unit.

16. The method of claim 15, the method comprising applying pressure to the biological fluid sample in the collection chamber to force flow of the biological fluid sample from the collection chamber into the waste reservoir through the filter.

17. A method wherein, having performed the steps of a method of claim 15, the method comprises the steps of
(i) isolating nucleic acids, proteins or cells from the biological material captured on the filter and/or in the solution if present; and
(ii) testing the isolated material for markers known to be associated with a particular disease, condition or disorder.

18. The method of claim 15, wherein the biological fluid is urine or a bladder wash, or is blood or serum.

19. The method of claim 15, wherein the disease is cancer.

20. The method of claim 19, wherein the cancer is a urinary or gynaecological cancer.

* * * * *

UNITED STATES PATENT AND TRADEMARK OFFICE
CERTIFICATE OF CORRECTION

PATENT NO. : 10,533,932 B2
APPLICATION NO. : 15/927015
DATED : January 14, 2020
INVENTOR(S) : Per Guldberg and Kenneth Eric Steven Page 1 of 1

It is certified that error appears in the above-identified patent and that said Letters Patent is hereby corrected as shown below:

In the Claims

In Claim 7, Column 27, Line 9, please insert --"the"-- between "The assembly of claim 1, wherein" and "filtration device".

Signed and Sealed this
Twenty-fourth Day of March, 2020

Andrei Iancu
*Director of the United States Patent and Trademark Office*